US012678075B2

(12) United States Patent
Berney

(10) Patent No.: US 12,678,075 B2
(45) Date of Patent: Jul. 14, 2026

(54) SENSOR ASSEMBLY

(71) Applicant: Analog Devices International Unlimited Company, Limerick (IE)

(72) Inventor: Helen Berney, Pennywell (IE)

(73) Assignee: Analog Devices International Unlimited Company, Limerick (IE)

( * ) Notice: Subject to any disclaimer, the term of this patent is extended or adjusted under 35 U.S.C. 154(b) by 427 days.

(21) Appl. No.: 18/312,327

(22) Filed: May 4, 2023

(65) Prior Publication Data

US 2024/0366124 A1 Nov. 7, 2024

(51) Int. Cl.
*A61B 5/145* (2006.01)
*G01N 27/02* (2006.01)
*G01N 27/327* (2006.01)

(52) U.S. Cl.
CPC ....... *A61B 5/14546* (2013.01); *G01N 27/026* (2013.01); *G01N 27/3272* (2013.01)

(58) Field of Classification Search
CPC .. A61B 5/14546; G01N 27/02; G01N 27/026; G01N 27/3272
See application file for complete search history.

(56) References Cited

U.S. PATENT DOCUMENTS

| 5,319,046 | A | 6/1994 | Kozulic et al. |
| 7,470,533 | B2 | 12/2008 | Xu et al. |
| 9,816,988 | B1 | 11/2017 | Paik et al. |
| 10,444,179 | B2 | 10/2019 | Paik et al. |
| 11,041,194 | B2 | 6/2021 | Clarke et al. |
| 11,065,615 | B2 | 7/2021 | Glezer et al. |
| 2004/0038426 | A1 | 2/2004 | Manalis |
| 2005/0026202 | A1 | 2/2005 | Edman et al. |
| 2005/0191687 | A1 | 9/2005 | Wang et al. |
| 2008/0035180 | A1 | 2/2008 | Mutharasan et al. |
| 2008/0092649 | A1 | 4/2008 | Chen |
| 2011/0031123 | A1 | 2/2011 | Schulze et al. |
| 2011/0036719 | A1 | 2/2011 | Neyts et al. |
| 2012/0142016 | A1 | 6/2012 | Ronaghi et al. |

(Continued)

FOREIGN PATENT DOCUMENTS

| CN | 111051885 A | 4/2020 |
| EP | 2196796 A1 | 6/2010 |

(Continued)

OTHER PUBLICATIONS

European Search Report issued in corresponding European Application No. 241174227.9 dated Oct. 16, 2024.

(Continued)

*Primary Examiner* — Dirk R Bass
(74) *Attorney, Agent, or Firm* — ArentFox Schiff LLP

(57) ABSTRACT

The present disclosure provides systems and method for determining a property of an analyte in a sample, the systems and methods use a sensor assembly comprising a sensing layer provided with through holes and a capture species configured to specifically bind with the analyte. The capture species is located adjacent and/or in the through holes such that analyte bound to the capture species can interact with the through holes of the sensing layer so as to alter the impedimetric property of the sensing layer. The sensing element provides a measurement signal which is indicative of an impedimetric property of the sensing layer and/or the sensing element comprises an IDE with at least a part of the sensing layer provided between electrodes of the IDE.

20 Claims, 7 Drawing Sheets

(56) References Cited

U.S. PATENT DOCUMENTS

| | | | |
|---|---|---|---|
| 2013/0270521 A1 | 10/2013 | Peng et al. |
| 2015/0377830 A1 | 12/2015 | Baldauf et al. |
| 2017/0226037 A1 | 8/2017 | Johnson et al. |
| 2017/0356904 A1 | 12/2017 | Paik et al. |
| 2019/0017954 A1 | 1/2019 | Shin et al. |
| 2019/0391142 A1 | 12/2019 | Jeon et al. |
| 2020/0200743 A1 | 6/2020 | Paik et al. |
| 2020/0271604 A1 | 8/2020 | Mohanty |
| 2020/0326297 A1 | 10/2020 | Paik et al. |
| 2021/0114025 A1 | 4/2021 | De Freitas Dias et al. |
| 2022/0196596 A1 | 6/2022 | Swett |
| 2022/0252542 A1 | 8/2022 | Merriman et al. |
| 2023/0097591 A1 | 3/2023 | Doris et al. |

FOREIGN PATENT DOCUMENTS

| | | |
|---|---|---|
| EP | 2488866 B1 | 4/2015 |
| JP | 2006-322878 A | 11/2006 |
| WO | 2009/035647 A1 | 3/2009 |
| WO | 2009/155423 A1 | 12/2009 |
| WO | 2013/192178 A1 | 12/2013 |
| WO | 2015/196148 A1 | 12/2015 |
| WO | 2018/078967 A1 | 5/2018 |
| WO | 2020/176793 A1 | 9/2020 |
| WO | 2022/232506 A1 | 11/2022 |

OTHER PUBLICATIONS

Extended European Search Report and Search Opinion received for European Application No. 24174226.1, mailed on Sep. 26, 2024, 8 pages.

Extended European Search Report and Search Opinion received for European Application No. 24174230.3, mailed on Oct. 21, 2024, 10 pages.

Extended European Search Report and Search Opinion received for European Patent Application No. 24174228.7, mailed on Sep. 16, 2024, 8 pages.

Extended European Search Report and Search Opinion received for European Patent Application No. 24174229.5, mailed on Oct. 29, 2024, 10 pages.

Gomes et al., "The increasing dynamic, functional complexity of bio-interface materials", Nature Reviews Chemistry, vol. 2, No. 3, Article No. 0120, Mar. 7, 2018, pp. 1-15.

Lu et al., "Plasmonic-Based Electrochemical Impedance Spectroscopy: Application to Molecular Binding", Analytical Chemistry, vol. 84, 2012, pp. 327-333.

Luo, Ruben, "Protein interaction analysis Guide to SPR Data Analysis on the ProteOn™ XPR36 System", Bulletin 6300, BIO-RAD Laboratories, Inc., 2013, 8 pages.

Non-Final office action received for U.S. Appl. No. 18/312,071, mailed on May 21, 2025, 30 pages.

Non-Final office action received for U.S. Appl. No. 18/312,113, mailed on Jun. 10, 2025, 19 pages.

Polonschii et al., "Complementarity of EIS and SPR to Reveal Specific and Nonspecific Binding When Interrogating a Model Bioaffinity Sensor; Perspective Offered by Plasmonic Based EIS", Analytical Chemistry, vol. 86, 2014, pp. 8553-8562.

Rich et al., "Chapter-1-The Revolution of Real-time, Label-free Biosensor Applications", Wiley, Label-Free Technologies for Drug Discovery, Dec. 14, 2010, pp. 1-25.

Sullivan et al., "A simulation and experimental study of electrochemical pH control at gold interdigitated electrode arrays", Electrochimica Acta, Article 139113, vol. 395, 2021, pp. 1-29.

Chatterjee et al., "Direct kinetic fingerprinting and digital counting of single protein molecules", PNAS research article applied biological sciences, vol. 117, No. 37, Sep. 15, 2020, pp. 22815-22822.

Deamer et al., "Three decades of nanopore sequencing", In Nature biotechnology, vol. 34, No. 5, May 6, 2016, pp. 1-18.

Supplementary European search report received for European Patent Application No. 16773620.6, mailed on Sep. 13, 2018, 10 pages.

Fologea et al., "Slowing DNA Translocation in a Solid State Nanopore", In Nano Letters, vol. 5, No. 9, Aug. 9, 2005, 15 pages (Abstract Only).

Fujimoto et al., "Effects of different cations on the hydrodynamic radius of DNA", Biophysical Journal, vol. 67, Jul. 1994, pp. 304-308.

Hamidabad et al., "Translocation through a narrow pore under a pulling force", Scientific Reports, vol. 9, Article No. 17885, 2019, pp. 1-12.

Keyser et al., "Direct force measurements on DNA in a solid-state nanopore", Nature Physics, vol. 2, Jul. 2006, pp. 473-477.

Kiaee et al., "A pH-Mediated Electronic Wound Dressing for Controlled Drug Delivery", Advanced Healthcare Materials, vol. 7, Issue 18, Sep. 19, 2018, 25 pages.

Laureyn et al., "Microelectronics-Based Biosensors for the Detection of Proteins and Nucleic Acids", Sensors for Environment, Health and Security, 2009, pp. 319-332.

Lee et al., "Implementation of force differentiation in the immunoassay", Analytical Biochemistry, vol. 287, 2000, pp. 261-271.

Mahmoodi et al., "Single-step label-free nanowell immunoassay accurately quantifies serum stress hormones within minutes", Science Advances, vol. 7, No. 27, Jun. 30, 2021, 9 pages.

Minnella, Walter, "pH control in microfluidics: a short review, Introduction to pH control in microfluidics", LAPASO project, Innovative Training Networks, 2023, pp. 1-5.

Modarres et al., "Phase-controlled field-effect micromixing using AC electroosmosis", In Microsystems & Nanoengineering, vol. 6, Article 60, Jul. 27, 2020, pp. 1-11.

Monteiro et al., "Measuring local pH in electrochemistry", Current Opinion in Electrochemistry, vol. 25, Feb. 2021, pp. 1-9.

Nikitin et al., "Magnetic Nanoparticle as a Tool for Remote DNA Manipulations at a Single-Molecule Level", ACS Applied Materials & Interfaces, Mar. 19, 2021, pp. S1-S17.

Pande et al., "Electrochemically Induced pH Change: Time-Resolved Confocal Fluorescence Microscopy Measurements and Comparison with Numerical Model", Journal of Physical Chemistry Letters, vol. 11, Jul. 28, 2020, pp. 7042-7048.

Purcell, E. M., "Life at low Reynolds number", Physics and Our World, 1977, 2 pages (Abstract Only).

Sadeghian et al., "Interdigitated electrode design and optimization for dielectrophoresis cell separation actuators", Journal of Electrostatics, vol. 86, Apr. 2017, pp. 41-49.

Sevenler et al., "Beating the reaction limits of biosensor sensitivity with dynamic tracking of single binding events", PNAS research article engineering, vol. 116, No. 10, Mar. 5, 2019, pp. 4129-4134.

Strunz et al., "Dynamic force spectroscopy of single DNA molecules", Proc. Natl. Acad. Sci., vol. 96, Sep. 1999, pp. 11277-11282.

Tropini et al., "Multi-Nanopore Force Spectroscopy for DNA Analysis", In Biophysical Journal, vol. 92, Issue 5, Mar. 2007, pp. 1632-1637.

Ying et al., "Nanopore-based technologies beyond DNA sequencing", Nature Nanotechnology, vol. 17, Nov. 2022, pp. 1136-1146.

Zeng et al., "Dynamic single-molecule sensing by actively tuning binding kinetics for ultrasensitive biomarker detection", PNAS, vol. 119 No. 10 e2120379119, 2022, pp. 1-7.

Jin Lu, et al., "Plasmonic-Based Electrochemical Impedance Spectroscopy: Application to Molecular Binding" NIH Public Access Author Manuscript, Anal Chem. Jan. 3, 2012; 84(1): 327-333. doi:10.1021/ac202634h.

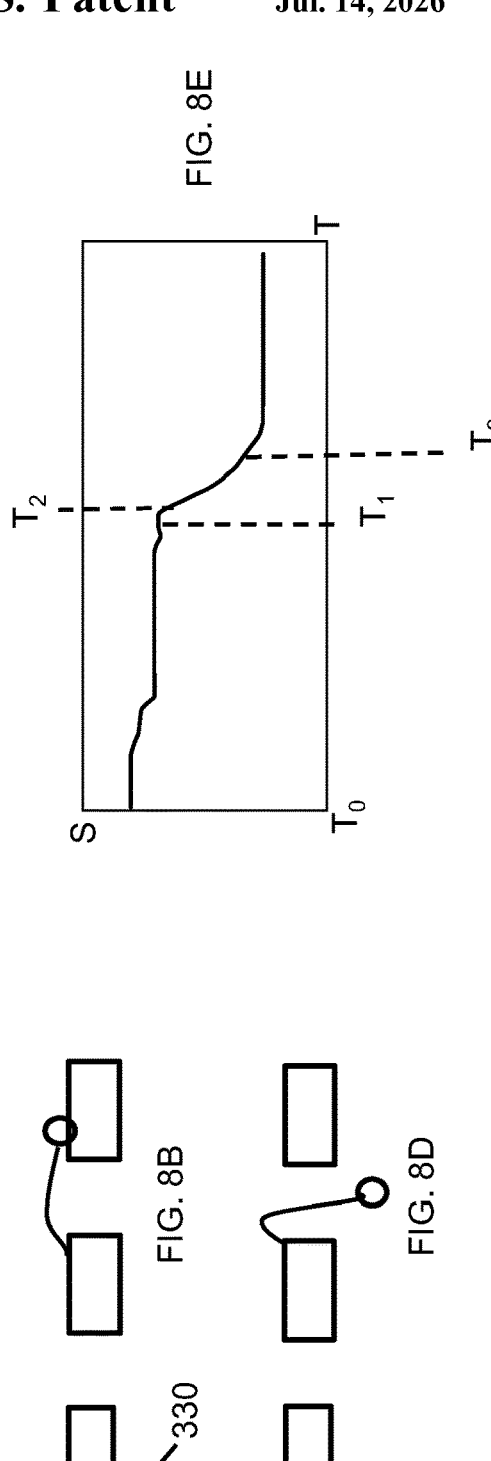
FIG. 8E
FIG. 8A
FIG. 8B
FIG. 8C
FIG. 8D
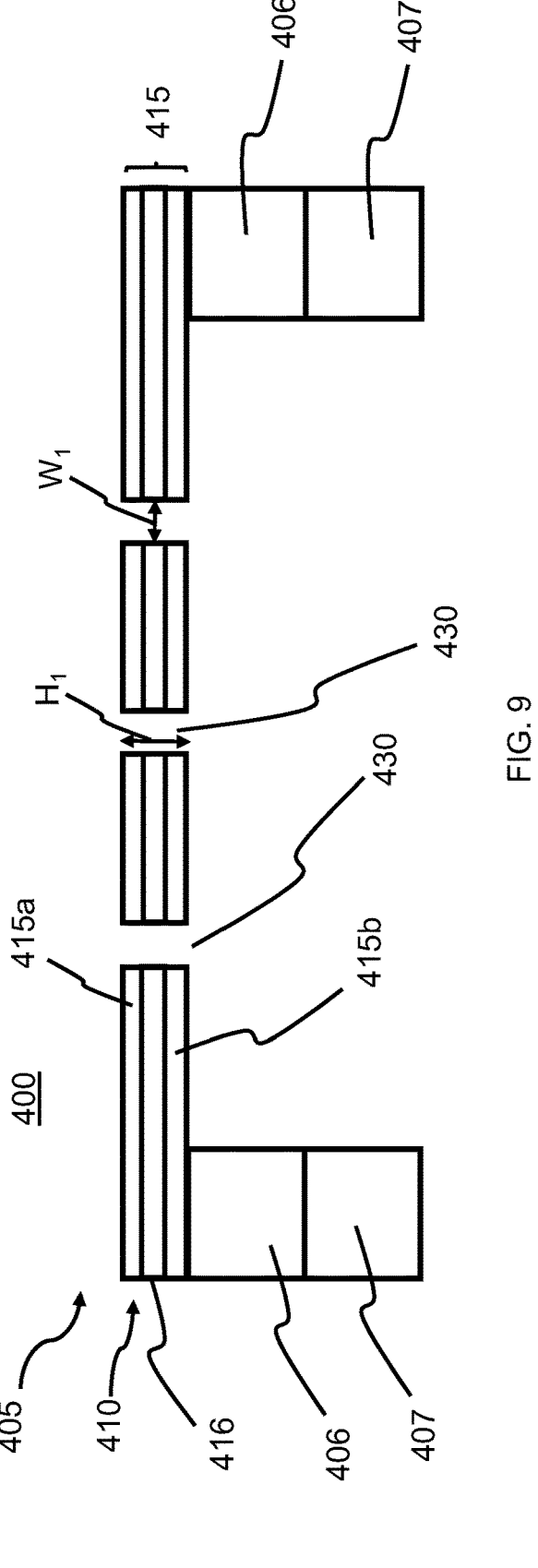
FIG. 9

SENSOR ASSEMBLY

FIELD OF THE DISCLOSURE

This disclosure relates to a sensor assembly, for example a biosensor or chemical assay, for determining a property of an analyte in a sample matrix, and a system and method for determining a property of an analyte in a sample matrix.

BACKGROUND

Various biological and chemical assay are known for sensing analytes. Analytes may, for example, include biomarkers, such as hormones, established to assist in patient monitoring and/or diagnosis.

Many of these assays are now carried out using electrical sensors, such as electrochemical sensors. For example, some traditional sensors in these fields use sensing elements with an immobilized capture species provided thereon. These are typically provided on the surfaces of the sensing elements through covalent chemical linkage, covalent-like interactions (e.g. chemisorption of anchor species onto the surface through chemical bond formation) and non-covalent-like interactions (e.g. physisorption of anchor species onto the surface through weaker, often van der Waals, interactions) depending on the identity of the surface and the anchor species. These species are used to capture target analytes, with the binding of analytes causing a change in a measured output (e.g. current). Typically these use direct current (DC) measurements, such as potentiometric or amperometric sensing.

Although rapid improvements in the selectivity and sensitivity of these sensors have been made over the past decades, there is still a need to improve these, particularly for biological sensing systems. For example, there is a desire to increase the accuracy of the detection of a particular analyte, particularly where other non-analyte species may interfere with the measurement. This can occur, for example, through non-specific binding of non-analyte species (e.g. absorption on the surface of the sensing element) which can interfere with the measurement signal. There can be interference in the form of non-analyte species inhibiting binding of the analyte to the capture species. These issues impact limits of detection, signal-to-noise and speed of measurement, for example. Such problems can be particularly problematic in biosensors, for example where biological fluids are used as the same (e.g. blood, saliva, etc) as these contains numerous species, including large species such as proteins and ion complexes.

More generally, there is a desire to obtain a measurement more quickly as time to binding can be slow. Often an incubation period is required, slowing down measurements and limiting applications (such as point-of-care testing).

SUMMARY OF THE DISCLOSURE

The present disclosure provides systems and method for determining a property of an analyte in a sample, the systems and methods use a sensor assembly comprising a sensing layer provided with through holes and capture species configured to specifically bind with the analyte. The capture species are located adjacent and/or in the through holes such that analyte bound to the capture species can interact with the through holes of the sensing layer so as to alter the impedimetric property of the sensing layer. The sensing element provides a measurement signal which is indicative of a impedimetric property of the sensing layer and/or the sensing element comprises an IDE with at least a part of the sensing layer provided between electrodes of the IDE.

In a first aspect, there is provided a system for determining a property of an analyte in a sample comprises: a sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface; and a capture species configured to specifically bind with analyte provided on the sensing layer; and a property determination unit configured to determine the property of the analyte. The sensing element is arranged in the fluid chamber such that sample can reside above the upper surface, reside below the lower surface and pass through the through holes in the sensing layer. The sensing element provides a measurement signal indicative of an impedimetric property of the sensing layer. The capture species are located adjacent and/or in the through holes such that analyte bound to the capture species can interact with the through holes of the sensing layer so as to alter the impedimetric property of the sensing layer. The property determination unit is configured to determine the property of the analyte based on the impedimetric property of the sensing layer indicated by the measurement signal.

In a second aspect, there is provided a system for determining a property of an analyte in a sample, the system comprising a sensor assembly comprising a sensing element. The sensing element comprises an interdigitated electrode (IDE) comprising a first electrode and a second electrode, the first and second electrodes arranged in an interdigitated configuration; a sensing layer arranged at least in part between the first electrode and second electrode of the IDE, the sensing layer comprising an upper surface and a lower surface and a plurality of through holes, each of the through holes extending from the upper surface to the lower surface; and capture species configured to specifically bind with the analyte provided on the sensing layer. The capture species are located adjacent and/or in the through holes such that analyte bound to the capture species can interact with the through holes of the sensing layer. The sensing element provides a measurement signal indicative of the interaction of the sensing element with the analyte.

In a third aspect, there is provided a method for determining a property of an analyte in a sample comprises providing a sensor assembly, the sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface, wherein the sensing element is arranged in the fluid chamber such that sample can reside above the upper surface, reside below the lower surface and pass through the through holes in the sensing layer; and capture species configured to specifically bind with analyte provided on the sensing layer, wherein the capture species are located adjacent and/or in the through holes such that analyte bound to the capture species can interact with the through holes of the sensing layer so as to alter a impedimetric property of the sensing layer. The method further comprises providing the sample to the sensing element, wherein at least a portion of analyte in the sample binds to the capture species to form specifically-bound analyte; obtaining a measurement signal indicative of the impedimetric property of the sensing layer from the sensing element; and determining the property of the analyte based on the impedimetric property of the sensing layer indicated by the measurement signal.

BRIEF DESCRIPTION OF THE DRAWINGS

The present invention will now be described in more detail with reference to the accompanying drawings, which are not intended to be limiting:

FIGS. 8A to 8D provide schematic cross-sectional views of a part of a system according to an embodiment;

FIG. 8E provides an example signal response; and

FIG. 9 provides a schematic cross-sectional plan view of a system according to an embodiment.

DETAILED DESCRIPTION

Figures 1, 2A:
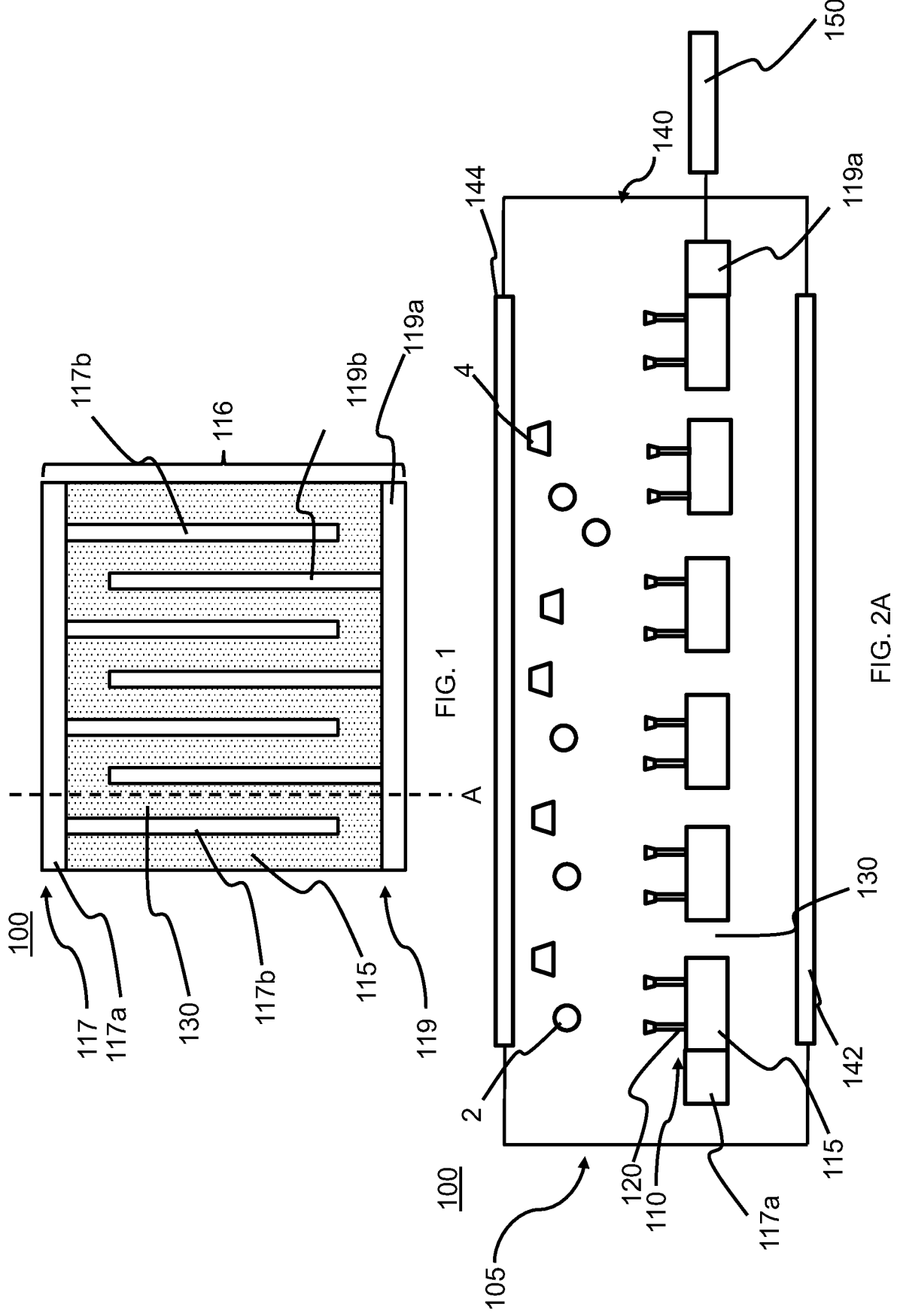
FIG. 1 provides a schematic plan view of a system according to an embodiment.
FIGS. 2A to 2E provide a schematic cross-sectional view of the system of FIG. 1.

Electrochemical sensors, including biosensors and chemisensors, are used for various biological and chemical assay are known for sensing analytes in samples. Analytes may, for example, include biomarkers, such as hormones, established to assist in patient monitoring and/or diagnosis.

Although rapid improvements in the selectivity and sensitivity of these sensors have been made over the past decades, there is still a need to improve the selectivity and sensitivity, particularly for biological sensing systems. Additionally, there is a desire to obtain a measurement more quickly as time to binding can be slow. Often an incubation period is required, slowing down measurements.

In a first aspect, a system for determining a property of an analyte in a sample comprises: a sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface; and capture species configured to specifically bind with analyte provided on the sensing layer; and a property determination unit configured to determine the property of the analyte. The sensing element is arranged in the fluid chamber such that sample can reside above the upper surface, reside below the lower surface sensing layer and pass through the through holes in the sensing layer. The sensing element provides a measurement signal indicative of an impedimetric property of the sensing layer. The capture species are located adjacent and/or in the through holes such that analyte bound to the capture species can interact with the through holes of the sensing layer so as to alter the impedimetric property of the sensing layer. The property determination unit is configured to determine the property of the analyte based on the impedimetric property of the sensing layer indicated by the measurement signal.

Such a system has been found to provide a selective, sensitive and flexible measurement platform for determining a property of an analyte.

The use of the sensing layer with through holes, or pores, provides a particularly useful tool for determining a property of an analyte. The configuration of the sensing layer and the capture species is such that analyte that is specifically bound to the (each) capture species is able to modify an impedimetric property of the sensing layer. As such, the relative position of the analyte within or around the through hole can have a significant effect on the measurement signal and can provide detailed information on the particular analyte, in addition to the information provided by the selective binding of the analyte to the capture species.

The sensing element is configured such that the impedance of the sensing layer (and in some embodiments other components of the sensing element, such as electrodes) is determined by the material properties of the sensing layer and, additionally, any component present in the through holes. Prior to interaction of the sensing layer with the sample, the impedimetric property of the sensing layer is determined by the sensing layer and any fluid within the through holes. However, once a species is received within through hole(s), the species will cause a change in this impedimetric property. Depending on the analyte property and its modulation of the signal the property to be measured may be due to double layer change or interruption, sensing layer thickness increase, faradaic or non-faradaic processes, transfer of charge, charge storage, or charge induction. For example, when an analyte is bound to the capture species and can interact with the through hole, such as enter and traverse through the through hole, the analyte (and/or a tag or detection species, which may enable the interaction with the through holes) will contribute to the impedimetric property of the sensing layer. Analytes tend to influence the impedimetric property by a significant margin as compared to a liquid (e.g. a sample matrix) and as such can create a response that is detectable by the system. For example, biomolecules have a permittivity of ~3 compared to a liquid, such as an aqueous solution, which typically have a permittivity of ~80. The response is also one that is directly related to the concentration of analyte (i.e. number of through holes filled and/or to the degree that they are filled), such that this can be used as a qualitative measurement.

Through holes are also particularly advantageous, as compared to other structures, as the signal generated provides significant additional information pertaining to the analyte and other species in the sample. For example, as compared to a flat surface or well, there is no lower bound which would otherwise truncate the response or interfere with manipulation. For example, there will be a specific response as the analyte passes through the through hole based on the analyte, size of the analyte, speed of movement, and this will enable the system to distinguish between the analyte and other components. This will also provide further information on other properties, such as concentration.

Moreover, the through holes can advantageously permit manipulation of the species in ways that can provide additional data and also permit flow through e.g. from the upper surface of the sensing layer to the lower surface of the sensing layer. For example, in some embodiments, a force (e.g. an electric field) may be applied in a direction that causes movement of species within the sample through the through holes. This can be, for example, non-specifically-bound components through the through holes, which will remove these from the sensing layer reducing noise and increasing accuracy. Moreover, this can be monitored in a way not otherwise achievable with closed structures, since the passage of non-specifically-bound species through the through holes can be monitored through changes in the measurement signal. In other examples, the analyte, whether bound or unbound (e.g. detached after binding), can be driven through the hole, causing further information on the interaction to be obtained. This movement can provide kinetic information, for example based on the rate of change (i.e. a temporal aspect), which in turn can provide further information, such as confirmation of the presence of analyte.

In a second aspect, a system for determining a property of an analyte in a sample comprises: a sensor assembly comprising: a sensing element. The sensing element comprises an interdigitated electrode (IDE) comprising a first electrode and a second electrode, the first and second electrodes arranged in an interdigitated configuration; a sensing layer arranged at least in part between the first electrode and second electrode of the IDE, the sensing layer comprising an upper surface and a lower surface and a plurality of through holes, each of the through holes extending from the upper surface to the lower surface; and capture species configured to specifically bind with the analyte provided on the sensing layer. The capture species are located adjacent and/or in the through holes such that analyte bound to the capture species can interact with the through holes of the sensing layer. The sensing element provides a measurement signal indicative of the interaction of the sensing element with the analyte.

As set out above, such systems provide a selective, sensitive and flexible measurement platform for determining a property of an analyte. The use of through holes in conjunction with capture species provides a selective means for probing a sample. Moreover, the present of the IDE enables the miniaturisation of the system by eliminating the need for a reference electrode. Typical systems require bulky reference electrodes or pseudo reference electrodes which can have performance problems. Together, these enable the provision of a miniaturised yet accurate sensing system.

In one embodiment of the second aspect, the capture species are located adjacent or in the through holes such that analyte bound to the capture species can interact with the through holes of the sensing layer so as to alter the impedimetric property of the sensing layer. In such an embodiment, the sensing element provides a measurement signal indicative of the impedimetric property of the sensing layer, and the system further comprises a property determination unit configured to determine the property of the analyte based on the impedimetric property of the sensing layer indicated by the measurement signal. In a further or alternative embodiment, the system further comprises a fluid chamber for receiving a sample, and the sensing element is arranged in the fluid chamber such that sample can reside above the upper surface, reside below the lower surface and pass through the through holes in the sensing layer.

The following embodiments apply equally to the first, second and third aspects disclosed herein.

Transduction

As set out herein, an impedimetric property is measured. In embodiments, the impedimetric property may be selected from a dielectric property (e.g. permittivity), resistance, capacitance, impedance, conductance, or a combination thereof. Depending on the analyte property and its modulation of the signal the property to be measured may be due to double layer change or interruption, sensing layer thickness increase, faradaic or non-faradaic processes, transfer of charge, charge storage, or charge induction. That is, the impedance gives an indication of the opposition to current flow, and this can be influenced by any one of these factors (amongst others). The interaction of an analyte (and the capture species) with the through hole will impact these features and therefore impact the impedimetric property. The changes which occur in the sensing element, particularly the sensing layer, are as a result of interaction with (e.g. occlusion of) the through holes and modulation of electrical phenomena, such as charge transfer, charge induction or current. The systems and methods can therefore determine capacitance, impedance and/or permittivity such that the measurement signal relates to at least one of these and use this to determine the property of the analyte.

The measurement can be performed using a combination of alternating current (AC) and direct current (DC) and the measurement can be performed at a single frequency or frequency range. In some embodiments, the measurement can be performed using AC measurements. For example, these can enable spectroscopic analysis (e.g. via electrical impedance spectroscopy (EIS)). Such measurements will typically take place over a predetermined frequency range chosen for the particular sensing layer (where the response is effectively linear) and using AC. Measurement of an impedimetric property, such as permittivity, can advantageously be achieved using AC parameters, rather than the traditional DC (only) measurements often used in electrochemical sensing. Use of these parameters over DC measurements alone can advantageously provide a more detailed picture of the response of the interaction with the analyte, and thus provide more information about the analyte itself.

In one embodiment, the impedimetric property is the impedance. This can be converted from measurements of e.g. resistance (the "real" component of the impedance) and reactance (the "imaginary" component of impedance) to capacitance, resistance, impedance, phase angle, using techniques and calculations known in the art.

In one embodiment, the impedimetric property is a dielectric property such as permittivity (i.e. relative permittivity or dielectric constant). Measurement of this can advantageously be achieved using alternating current (AC), rather than the traditional direct current (DC) measurements often used in electrochemical sensing. The dielectric property of the sensing layer is determined by the permittivity of the material from which the sensing layer is formed and, additionally, any component present in the through holes. Prior to interaction of the sensing layer with the sample, the permittivity of the sensing layer is determined by the sensing layer and any fluid within the through holes. Typically this will be a liquid, such as an aqueous solution, which typically have a permittivity of ~80. However, once a species is received within through hole(s), the species will cause a change in this permittivity. For example, when an analyte is bound to the capture species and can interact with the through hole, such as enter and traverse through the through hole, the analyte (and/or a tag or detection species, which may enable the interaction with the through holes) will contribute to the dielectric property of the sensing layer. The permittivity of analytes tends to be an order of magnitude different to that of a liquid sample matrix and as such can create a response that is detectable by the system. For example, biomolecules have a permittivity of ~3. The response is also one that is directly related to the concentration of analyte (i.e. number of through holes filled and/or to the degree that they are filled), such that this can be used as a qualitative measurement.

In one embodiment, the system is configured to measure impedance using electrochemical impedance spectroscopy (EIS). The measurement signal can therefore be an AC signal which can be processed to provide data on the analyte.

Such a measurement can be limited to small potentials thereby limiting the excitation frequencies where a response is essentially linear, and thus providing a more accurate measurement than can be achieved using DC measurements alone. For example, DC in liquid is limited to a voltage below the water (or carrier) electrolysis voltage. In such an embodiment, this can be achieved by addressing the sensing element, and specifically an electrode of the sensing element, using an AC.

Sensing Element

The sensing element (or "sensing device") provides the measurement signal and therefore may be addressable to provide the measurement signal. For example, the sensing element comprises a sensing layer and may further comprise an electrode, which electrode may be addressable to provide the measurement signal. Where there are plural electrodes, each may be individually addressable. The electrode(s) may be formed by an electrode layer provided in contact with (on or abutting) the sensing layer, and in some embodiments may be embedded within the sensing layer.

Sensing Element—Sensing Layer

In some embodiments, the sensing layer may comprise or be a dielectric layer. In embodiments, the dielectric layer may comprise or be a polymer layer, a glass layer, a glass-ceramic layer, a ceramic layer, a metal oxide layer, a metal nitride layer, a silicon-based layer or combinations thereof. In certain embodiments, the dielectric layer comprises or is a polyimide, silicon dioxide, or silicon nitride layer. In some embodiments, the sensing layer is a nanoporous membrane, with the nanopores forming the through holes (structures) on the nano-scale (e.g. 1 to 1000 nm, or 1 to 100 nm). The measurement can depend on an impedance property e.g. on the permittivity and/or capacitance of the layer. This may then further comprise an electrode layer provided in contact with (e.g. on or abutting) the sensing layer. In one further embodiment, the electrode layer may be embedded within the sensing layer.

The sensing layer may be comprised of a single layer of material on or in which the through holes are formed. Alternatively, or additionally, this may comprise plural layers in a stacked arrangement with the through hole extending from the upper surface of the uppermost layer to the lower surface of the lowermost layer. In some embodiments, the layer may comprise plural coplanar layers, where the layers are adjacent to one another and form through hole(s) therebetween (i.e. with the through hole extending in the gap between the two layers). An electrode may be formed as part of the sensing layer such that the sensing layer comprises this, in which cases the through holes may also extend through the electrode(s), or the sensing element may comprise this as a separate component.

In one embodiment, the one or more through holes have a largest diameter of less than or equal to 2 μm and a depth of less than or equal to 2 μm. By largest diameter, it is meant that the width at the widest point. This may be at one of the upper or lower surfaces of the sensing layer.

In one embodiment, the one or more through holes have a largest diameter (at their widest point) less than or equal to 2 μm, for example from 50 nm to 1 μm. In some embodiments, the through holes have a diameter (at their widest point) of less than or equal to 1000 nm, for example less than or equal to 800 nm, less than or equal to 500 nm. This may be from 1 nm to 2000 nm, 1 nm to 1000 nm, 1 nm to 800 nm, 1 nm to 500 nm, such as 10 nm to 1000 nm, 10 nm to 800, 10 nm to 500 nm, 50 nm to 2000 nm, 50 nm to 1000 nm, 50 nm to 800, 50 nm to 500 nm, 100 nm to 1000 nm, 100 nm to 800, or 100 nm to 500 nm. In one embodiment, the through holes have a narrowest diameter of at least 0.5 nm, for example at least 1 nm, or at least 10 nm. Through hole radius will impact the response to an analyte: a larger through hole will have a response which is more dependent on the materials within it. A smaller through hole may be selective to particular analytes. Smaller holes have also been found to provide a higher electric field (field confinement), increasing sensitivity.

In embodiments, the sensing layer has a thickness of less than or equal to 2000 nm, such as less than or equal to 1000 nm, for example less than or equal to 800 nm, less than or equal to 500 nm. This may be 1 nm to 1000 nm, 1 nm to 800 nm, 1 nm to 500 nm, such as 10 nm to 1000 nm, 10 nm to 800, 10 nm to 500 nm, 50 nm to 1000 nm, 50 nm to 800, 50 nm to 500 nm, 100 nm to 1000 nm, 100 nm to 800, or 100 nm to 500 nm. Accordingly, in some embodiments where the through holes extend through the sensing layer (only), the through holes have a corresponding depth. In other embodiments, the depth of the through hole may be defined by plural layers, such as an electrode, such as the sensing element as a whole.

In some embodiments, the depth of the through hole may be less than or equal to 2 μm, for example less than or equal to 1000 nm, for example less than or equal to 800 nm, less than or equal to 500 nm. In one embodiment, the one or more through holes of each of the plurality of sensing sites have a depth of from 100 nm to 2 μm. This may be 1 nm to 1000 nm, 1 nm to 800 nm, 1 nm to 500 nm, such as 10 nm to 1000 nm, 10 nm to 800, 10 nm to 500 nm, 50 nm to 1000 nm, 50 nm to 800, 50 nm to 500 nm, 100 nm to 1000 nm, 100 nm to 800, or 100 nm to 500 nm. Exemplary combinations include a diameter of 1 nm to 1000 nm and a depth of 1 nm to 1000 nm, such as 10 nm to 500 nm and 10 nm to 500 nm depth. In one embodiment, the depth of the through hole is from 0.15 μm to 1 μm. Across these depths, noticeable changes in electric field strength and responses have been found, without causing significant variation of electric field across each individual sensing site. The depth can be measured from the upper surface of the sensing layer to the lower surface of the sensing layer.

In one embodiment, the sensing layer comprises a plurality of through holes, and wherein the through holes are spaced apart by at least 200 nm, at least 500 nm, at least 1000 nm, or at least 2 μm. In some embodiments, this may be from 200 nm to 30 μm, for example from 1 μm to 20 μm, from 2 μm to 20 μm or from 4 μm to 20 μm. These ranges have been found to provide a useful range in which the electric field can vary without impacting performance. It has been found in particular that increasing the through hole spacing from ~50 nm increases the electric field, thus increasing specificity, without reducing molecular transport efficiency. This increase is particularly fast in the range up to 5 μm, after which it levels off. The higher field provided is beneficial but with there are diminishing returns as transport becomes less efficient. Accordingly, the ranges recited herein are particularly effective.

At this size, and particularly the diameter, the analyte can have a significant effect on the impedimetric property. Moving analyte in and out of the through holes will therefore provide a significant response, thereby providing additional information as compared to simply receiving analyte on a surface. Movement within and around the through holes can be facilitated by the capture species, which may be bound to the sensing element (in some embodiments, the sensing layer) adjacent and/or in the through holes, for example by being anchored by a part of the capture species at a point adjacent (e.g. next to or abutting the through hole) or in the through hole.

In some embodiments, the sensing layer has been 1 and 1000 through holes, such as 1 to 500 through holes, such as 1 to 20, 1 to 100, 1 to 500, 2 to 20, 2 to 100 or 2 to 500 through holes.

The density (e.g. the number per unit area) of through holes present in the sensing layer will impact the response to the presence of an analyte. In some embodiments, the through holes may define at least 2% of the surface area of each the upper surface and/or lower surface of the sensing layer contributing to the measurement signal, for example at least 5%, at least 10%, at least 20%. A maximum surface area may be 40%. By "contributing to", this may in embodiments refer to the sensing layer located between (e.g. directly between) electrodes used to determine the measurement signal. Measurement may be carried out using SEM or TEM, for example.

In one embodiment, the sensing layer comprises a plurality of through holes having a largest diameter of less than or equal to 1000 nm, such as from 100 nm to 1000 nm, a depth of from 100 nm to 2 μm, such as 100 nm to 1 μm, and wherein the through holes are spaced apart by a spacing of from 1 μm to 20 μm, such as 2 μm to 10 μm.

The through holes may have any shape. For example, the through hole may have a cylindrical shape (e.g. with substantially circular or circular openings) or may take the form of tapered openings, channels or slits.

In some embodiments, the sensing layer may further comprise seal layer may be provided on top of the sensing layer, with the through holes extending through the seal layer to allow for sample provided to the sensing element to pass through the sensing layer. The seal layer may be, in some embodiments, an oxide layer or high dielectric constant (k) dielectric layer (e.g. high relative to silicon dioxide). The seal layer may have a thickness of from 1 nm to 10 nm, such as 1 to 5 nm, such as 2 to 4 nm.

Sensing Element—Electrode

In some embodiments, the sensing element comprises an interdigitated electrode (IDE). This can comprise a first electrode and a second electrode, the first and second electrodes arranged in an interdigitated configuration and at least a part of the sensing layer is arranged at least in part between the first electrode and second electrode of the IDE. The IDE is therefore provided with at least a part of the sensing layer between the interdigitated portions of electrodes of the IDE, and therefore at least some of the through holes are located between the interdigitated portions of the electrodes. This enables the miniaturisation of the system by eliminating the need for a reference electrode, without sacrificing or reducing the accuracy of the system, enabling use in point-of-care situations.

By interdigitated configuration, it is meant that the first electrode and second electrode are interdigitated with at least one of the electrodes surrounding at least a part of the other. In some embodiments the first electrode may comprise or be defined by plural extension portions (e.g. fingers) which are interlaced or interlocked with at least one, but optionally plural, extension portions (e.g. fingers) of the second electrode. For example, the first electrode may comprise at least first and second extension portions which are spaced apart from one another to form a recess therebetween and the second electrode comprises at least one first extension portion which is received in the recess. In embodiments, example IDE configurations may include interdigitated comb, spiral or serpentine configurations.

The spacing of the electrodes of the IDE can impact sensitivity. In an embodiment, the first and second electrodes in the interdigitated configuration can be spaced apart from one another by a spacing of from 10 nm to 10 μm, such as from 100 nm to 10 μm, from 500 nm to 10 μm, or from 100 nm to 5 μm. This may be that the extension portions are spaced apart by (e.g. the recess has a width of) 10 nm to 10 μm (such as from 100 nm to 10 μm, from 500 nm to 10 μm, or from 100 nm to 5 μm), with the sensing layer provided therebetween. This spacing is thought to provide an optimal sensitivity, at least because the change in content of the through holes will have a significant impact on measurement signal at this scale.

In embodiments, the IDE is at least partially embedded within the sensing layer. For example, the sensing layer may comprise a layer surrounding at least a portion of the electrodes (or extension portions of the IDE). The through holes may extend between the extension portions of the electrodes of the IDE.

Additionally or alternatively, in certain embodiments, the sensing layer may comprise an electrode which is addressable to provide the measurement signal. In some embodiments, there may be plural electrodes.

In embodiments, the electrodes disclosed herein (e.g. the IDE, such as the first and second electrode of the IDE) may be formed from or comprise metals, metal oxides, metal nitrides, carbon-based materials, a conductive polymer, doped silicon or polysilicon or combinations thereof. In an embodiment, the electrodes may be formed from or comprise gold, silver, copper, platinum, nickel, titanium, titanium nitride, ruthenium, ruthenium oxide or combinations thereof.

In further embodiments, the electrode(s) (e.g. of the IDE) may further comprise a plurality of through holes. For example, the electrode layer may also comprise a plurality of recesses or through holes. These may have the same or different properties to the sensing layer. The features set out herein for the structures of the sensing layer, such as structure and dimensions, apply equally to the electrode layer. Such through holes may also produce a response when interacting with analyte.

Sensing Element—Capture Species

The methods, systems and sensor assemblies disclosed herein can be used to determine or measure a property of an analyte in a sample, such as an analyte characteristic. In certain embodiments, this can be selected from the concentration of the analyte in the sample, the diffusion constant of the analyte (e.g. rate of diffusion measured in $m^2/s$) in the sample matrix, or a combination thereof. The terms "analyte concentration" or "concentration of the analyte" as used herein may, in certain embodiments, refer to the activity of the analyte. The activity of the analyte may provide a measure of the effective concentration of the analyte in a sample matrix.

The analyte may, for example, be selected from a molecular species, a metal ion, a virus, and a microorganism. Biomolecule analytes are particularly useful and may, for instance, be a hormone selected from an eicosanoid, a steroid, an amino acid, amine, peptide or protein, a nucleic acid, single or double stranded DNA, peptide nucleic acid.

Any suitable analyte capture species can be selected, according to the analyte which is intended to be sensed by the sensor assembly. For example, the capture species may comprise an antibody with specificity for a particular antigen. In such an example, the analyte may take the form of the antigen. More generally, the capture species may, in some embodiments, comprise at least one selected from a protein, a peptide, a carbohydrate, a nucleic acid, and an aptamer. The protein may, for example, be an enzyme, such as an enzyme having specificity for the analyte. In other non-limiting examples, the protein is an antibody. In the latter case, the analyte may be an antigen which is specifically bound by the antibody. The capture species may, for instance, comprise or be defined by an antigen. In this case, the analyte may be a species, such as an antibody, which is specifically bound by the antigenic capture species. The antigen may be or comprise, for example, a protein, a peptide, a carbohydrate, such as a polysaccharide or glycan.

The capture species (i.e. a plurality of individual capture species) may be located adjacent to (i.e. next to or abutting) and/or in the through holes of the sensing layer such that analyte bound to the capture species can interact with (e.g. move into and/or through) the through holes so as to alter the impedimetric properties of the sensing layer. The capture species may therefore surround each of the through holes, in some embodiments. In embodiments, the capture species are provided on the sensing layer, for example, these may be bound to the sensing layer. The capture species may be provided on the upper and/or lower surfaces of the sensing layer. In some embodiments, the sensing element is functionalized with the capture species. Such functionalization can be achieved in any suitable manner, such as by covalently or non-covalently immobilizing the capture species to the surface. In some embodiments, the capture species may be configured to permit movement of specifically-bound analyte through and out of the through holes. The capture species may be of sufficient length and/or flexibility to permit this and/or the through hole length can be chosen to enable this.

The captures species may be a rigid or flexible species. In some embodiments, the capture species binds to the analyte via a capture moiety and is configured so that this moiety is moveable relative to the sensing element. In this way, the analyte can move relative to the sensing element under the action of a sufficiently strong force (e.g. electric field). This may be as a result of the capture species being a flexible species. For example, the capture species may comprise a first portion bound to a surface of the sensing element and a second portion comprising the capture moiety, the two portions separated by a flexible linker. Flexibility in this regard is sufficient such that a bound analyte can be moved into an adjacent through hole or, wherein provided in the through hole (e.g. anchored therein) such that it can move in and out of the through hole. In some embodiments, the capture species comprises a DNA linker, the linker comprising a chain length of at least 24 nucleotides (nt), such as at least 25-nt, such as at least 30 nt. In some embodiments, the capture species comprises a double stranded DNA linker, the linker comprising a chain length of at least 24 base pairs, such as at least 25 base pairs, such as at least 30 base pairs.

In an embodiment, the analyte capture species comprises an aptamer. An aptamer may be defined as an oligonucleotide or peptide configured to bind the analyte. Such an aptamer may, for example, be configured to interact with, for example bind, various analyte types, such as small molecules, for example amino acids or amines, proteins, metal ions, and microorganisms.

One commonly used assay type is enzyme-linked immunosorbent assay (ELISA). ELISA is used for quantifying analytes such as peptides, proteins, antibodies, and hormones. These use a recognition element for selectively (specifically) interacting with, for example binding, the analyte of interest. The recognition element is immobilized on a suitable support. For example, an antigen is immobilized on the support and then complexed with an antibody that is linked to an enzyme. In biosensors and assays, such as ELISA, the non-specific binding of analyte and non-analyte species to the sensing element can result in low signal-to-noise ratio or high limits of detection (e.g. due to non-specific binding). Particularly in biological assays such as ELISA, the size of the species within a sample which non-specifically bind to the surface can also interfere with specific binding of the analyte to the capture species, slowing down the measurement process or even causing the sensor assembly to fail.

In some embodiments, a detection species may be provided to the sample, the detection species specifically-binding to the analyte. The detection species may be provided when the analyte is specifically bound to the capture species or before this occurs. The detection species may be an amplification species for amplifying the measurement signal or response, or may be a different species, for example provided with the purpose of increasing the selectivity of the measurement. This can in embodiments be as part of a sandwich assay. In some embodiments, the systems and methods disclosed herein use a sandwich ELISA method of detecting a property of an analyte, with the capture species being a capture antibody, the detection species being a detection antibody which may comprise double stranded DNA provided thereon. The DNA may be bound to the detection antibody via a linker, such as streptavidin and biotin. Use of the double stranded DNA in such a system is particularly useful as it is negatively charged and hence is susceptible to manipulation in an electric field.

The detection species can also be used as a means to providing the signal. Although in some embodiments movement of the specifically-bound analyte can be achieved using a flexible capture species, additionally or alternatively, the detection species may provide a flexible or additional flexible component which can be used achieve a response under the manipulation force. For example, in some embodiments, the analyte may be bound to the surface of capture species with the detection species bound thereto, and the detection species may be moved so as to interact with the through hole. This may provide the interaction of the analyte with the through hole. Moreover, the detection species in some embodiments may be detached from the analyte as part of the manipulation or detachment steps, which can provide further information.

More generally, the sensing element is arranged to receive a sample matrix. Sample matrix refers to the sample as a whole, including the analyte if present. Thus, it may comprise a carrier (such as a liquid) and the analyte. The sample matrix may be, for example, blood, urine, sweat, tears, etc., and may (potentially) contain the analyte. In an embodiment, the sample matrix is a liquid.

Sample Manipulation

In some embodiments, the system may further comprise a sample manipulation device for manipulating analyte and/or non-analyte species on the sensing element; and a control unit configured to operate the sample manipulation device.

In one embodiment, the control unit is configured to operate the sample manipulation device so as to apply a force to the sample sufficient to move specifically-bound analyte on the sensing element (in a "manipulation step") and the property determination unit is configured to determine the property of the analyte in the sample based on the measurement signal during and/or after the control unit operates the sample manipulation device to move specifically-bound analyte. In an embodiment, the sample manipulation device is configured to cause specifically-bound analyte to enter the through holes of the sensing layer.

In one additional or alternative embodiment, the control unit is further configured to operate the sample manipulation device so as to apply a force to the sample sufficient to detach specifically-bound analyte on the sensing element and thereby detach at least a portion of specifically-bound analyte on the sensing element (in a "detachment step") and the property determination unit is configured to determine the property of the analyte in the sample based on the measurement signal during and/or after the control unit operates the sample manipulation device to detach specifically-bound analyte. In some embodiments, the sample manipulation device is configured to cause specifically-bound analyte to detach and pass through the through holes of the sensing layer.

Manipulation and detachment steps can be used to obtain further information about the analyte, including the interaction of analyte with the through holes of the sensing layer. This can be monitored over time to build up an interaction picture and provide further information on the analyte. For example, the kinetics of movement or the specific interactions could be used as a fingerprint indicative of the presence of the analyte and a quantity of the analyte. For example, the response may vary based on the speed of movement or interaction with the through holes based on the size and nature of the analyte.

In some embodiments, the control unit is configured to operate the sample manipulation device to generate an electric field so as remove any non-specifically-bound analyte and/or non-analyte species but retain specifically-bound analyte on the sensing element (in a "removal step"). The property determination unit is configured to determine the property of the analyte based on the measurement signal after operation of the sample manipulation device to remove the non-specifically-bound species. The property determination unit may also determine a sample baseline measurement based on the measurement signal before and/or during operation of the sample manipulation device. This can be used in compensating for non-specifically-bound species (e.g. in future measurements) or to determine the parameters for the removal step.

The removal step can provide significant sensitivity improvements by reducing the signal-to-noise ratio (SNR) by stripping away at least a portion of the non-specifically-bound species from the surface(s) of the sensing element and thereby reducing the interference from these on the measurement signal. The ultimate measurement will be more accurate and limits of detection are reduced. Moreover, the removal step can also have the benefit of improving the response time of the sensor. Non-specific binding on a sensing element can lead to interference with specific binding processes and require longer incubation times. By disrupting species that are non-specifically-bound, this interference is removed. Using an electric field to perform a removal step avoids drawbacks associated with other methods which seek to avoid non-specific binding, such as having to test different blocking buffers, blocking layers or capture species.

The forces used in the steps disclosed above can be provided by any suitable means of generating a force which acts on the species to move them within the sample matrix on the sensing layer. For example, in some embodiments, this can be through the use of an electric field, magnetic field, ultrasound energy, thermal gradients, osmotic gradients, density gradients, and/or a fluid flow. In some embodiments, the force is provided by at least one of an electric field or a magnetic field (this may include an electromagnetic field), and may include both. Accordingly, in some embodiments, the sample manipulation device comprises a plurality of electrodes configured to apply an electric field about the sensing element. In other embodiments, thermal gradients, osmotic gradients and/or density gradients can be used, for example by two different regions having different properties above and below the sensing layer to drive movement from one region to the other (e.g. from one side of the sensing layer, through the through holes, to the other side).

In some embodiments, the capture species and/or analyte may comprise an amplifying element responsive to the force, such as electric and/or magnetic fields, where used, such as electro-active element or moiety or a magnetic-active element or moiety. The amplifying element can increase the response of the capture species to the force used to manipulate the analyte and provide useful kinetic data. This can also enable manipulation where the capture species and/or analyte would otherwise not permit manipulation (e.g. due to no charge). Alternatively or additionally, the amplifying element can increase the influence on the measurement signal, for example the amplifier element may causing increase the change in impedance of the sensing element. In some embodiments, the amplifying element may comprise a polymer or a metal, such as a metallic bead (such as a magnetic bead).

In embodiments of the systems and methods disclosed herein, the strength or intensity of the force (e.g. electric field) is varied (e.g. by the control unit). This can be during each of the removal, manipulation and/or detachment steps. In other words, the strength or intensity of the field providing the force is varied. This will provide a different effect and response than if a single value force is applied and, if measurements are recorded, can generate additional information on the types of non-specific binding or the state of the sensor assembly. For example, force may vary between a minimum and a peak or maximum strength, the peak strength being a strength which is sufficient to remove non-specifically-bound species from at least a portion of the sensing element but has a strength less than that required to detach specifically-bound analytes from the sensing element.

In some embodiments, this variation of the force field may be selected so as to cause movement of the species within the sample matrix in a single direction. For example, changing from a first value imparting a first directional movement to a second value imparting the same directional movement could be used (e.g. the application of a first positive voltage across the electrodes generating an electric field followed by a second positive voltage, or the inverse (negative to negative)). This can be so as to drive species back and forth through the through holes, for example.

In other embodiments, the variation may be selected so as to cause movement of the species within the sample matrix in plural directions, for example opposite directions. For example, the application of a first positive voltage across the electrodes generating an electric field followed by a second negative voltage, or the reverse. These can be used to further interrogate the measurement signal and may improve removal depending on the nature of the binding on the surface. Where opposing directions are cycled, numerous methods within these can be utilized to ensure removal away from the sensing element if required, such as additional applications in one direction, or asymmetric intensities or durations of the application of the electric field. This can be used to move species into and out of contact with the through holes, for example back and forth through the through holes.

Detaching the analyte from the capture species (e.g. in a detachment step) or a tag or detection element from the analyte requires a force to be applied which is sufficient to overcome the strength of the interaction between these elements. This force applied will depend on the properties of the species it is acting on (e.g. net electric charge where e-filed is used), and the force required to detach the relevant species will depend on the interaction between the species, such as strength of the bond. These forces are typically in the range of 10 to 400 pN, such as 30 to 400 pN, such as 30 to 300 pN. Accordingly, in embodiments, during a detachment step, the force applied to the bound analyte is from of 10 to 400 pN. The force applied during the other steps, such as manipulation or removal steps, can accordingly be less than this, such as less than or equal to 50 pN, less than or equal to 40 pN, less than or equal to 30 pN or less than or equal to 10 pN. It will be appreciated that a higher force can be applied during manipulation or removal steps where the binding between the analyte and other species is higher. For example, where a 140 pN force is required to detach an analyte from a capture species, the force applied during manipulation or removal steps may be less than or equal to 100 pN.

The removal step may be carried out for at least 0.1 ms, such as at least 5 ms, 10 ms, at least 50 ms or at least 100 ms. This can be 0.1 ms to 5 minutes, for example. The manipulation or detachment steps, where present, may be carried out for 0.1 ms, such as at least 5 ms, 10 ms, at least 50 ms or at least 100 ms, at least 1s or more. This can be 0.1 ms to 5 minutes, for example. Where the steps noted above are alternated/cycled (and may further include periods between where none occurs), the total period may be 0.1 ms to 30 minutes, such as 0.1 ms to 10 mins, 0.1 ms to 5 mins, 1 ms to 5 mins or any suitable range therebetween. An incubation step, where present, may be carried out for at least 5 s, such as at least 60 s. This can be up to 30 mins, or up to 10 mins, for example.

Electric Field

In embodiments, an electric field is used to provide the force for manipulating the species in the sample matrix (e.g. during the manipulation, detachment and removal steps disclosed above) and therefore an electric field is configured so as to move the relevant species in question. That is, it is arranged relative to the sensing element (e.g. adjacent and so that the electric field can influence sample on the sensing element (this may be so that the field overlaps with at least one surface of the sensing element or has sufficient force to create a movement on the surface of the sensing element)) and with the required intensity or strength. For example, in the removal step, the field has a strength or intensity that is sufficient to remove non-specifically-bound components from at least a portion of (or in some embodiments all) of the sensing element but less than that required to detach specifically-bound analytes from the sensing element (a force which is lower than the force corresponding to the affinity between an individual capture species and an analyte (e.g. an individual analyte molecule)).

In embodiments of the systems and methods disclosed herein, the strength or intensity of the electric field is varied (e.g. by the control unit), for example as measured by the input voltage (V/m or mV/m). For example, the electric field may vary between a minimum and a peak or maximum strength. This can be achieved by varying the voltage across the electrodes used to generate the field, for example, or could be achieved by other means such as moving the relative position of the electrodes.

In some embodiments, the strength or intensity of the fields may provide a force during manipulation or detachment step that is at least 1.5 times stronger than the force provided by the electric field used in the removal step, for example at least 2 times, at least 3 times. This may be by the field strength or intensity being at least 1.5 times stronger than the intensity or strength provided by the electric field used in the removal step, for example at least 2 times, at least 3 times.

In alternative or additional embodiments, the electric field may be varied between positive and negative input voltages so as to vary the properties of the electric field.

In embodiments, the electric field may be varied by at least one of the following methods: a linear ramp or sweep where the intensity is increased at a steady rate (e.g. 1 mV/m/s), a non-linear ramp or sweep where the intensity is increased at varying rate(s), at least one step change increase, or combinations thereof. Each can be between the whole range or a part of the range between the minimum and maximum. Where it is the former, these can be combined in a single step of varying. Alternatively, each could be employed in multiple separate applications of an electric field. Each may lead to a different response thereby providing different information on the non-specific binding. For example, different approaches may lead to different detachments and/or interactions between the sensing layer and the species.

In embodiments incorporating a removal step and/or manipulation steps may comprise cycling the electric field between at least two strengths or intensities. In one embodiment, this can be between on and off. In other embodiments, this may be between cycled between at least two values. In some embodiments, this may be values imparting only a single direction of movement on the species (e.g. a field in the same direction, for example between two fixed electrodes and of the same polarity). In other embodiments, the values may impart different directions, such as opposing directions of movement on the species (e.g. different fields in different directions, for example between two fixed electrodes in which the polarity is switched).

Such methods can be used to obtain additional information about the non-specifically-bound species, which can be further used to improve the knowledge about the non-specific binding species. For example, rate of change in the measurement signal could be monitored. This can in turn be used in compensating for the non-specific binding.

It will be appreciated that in any of the embodiments mentioned here, although the resultant force of the electric field acting on a particular component (e.g. the analyte or non-analyte species) will depend on a number of factors, including the charge on the component, the magnitude of the force will be determined by the magnitude of the electric field such that a higher V/m value will lead to a greater force acting on the species in the sample.

Generation of the electric field can be achieved by applying a voltage across a first electrode and a second electrode located adjacent to (i.e. next to or abutting) the sensing element. The sample (e.g. fluid, such as a solution) can be received between the electrodes.

In embodiments, during a removal step, the voltage across the first electrode and second electrode selected from −750 mV to 750 mV. For example, in certain embodiments, the voltage (i.e. potential difference) can be −500 mV to 500 mV, 0 to 500 mV, or −350 mV to 350 mv, such as 0 to 350 mV. As set out above, this can be at least one discrete value within these ranges, of may comprise a ramp or step through these ranges. Where an electric field is used in a manipulation or detachment step, the voltage used to generate the field may be at least 500 mV, at least 750 mV, at least 1V. For example 500 mV to 10 V, such as 1V to 5V.

The forces used e.g. in the detachment step, can be provided by generating an electric field using the voltages mentioned above, for example, particularly in or immediately adjacent the through holes which will provide an electric field concentrating structure (e.g. at the edges of the through holes). As noted above, the force applied will depend on the net electric charge of the species it is acting on. This force applied will depend on the net electric charge of the species it is acting on. For example, in some embodiments, the electric field may require a strength of from $0.5\times10^6$V/m to $1\times10^8$ V/m, such as $1\times10^6$ V/m to $2\times10^7$ V/m. This may be present in the localised regions around the through holes and need not be throughout the entire applied field.

In some embodiments, other parameters of the electric field are varied, such as frequency.

In one embodiment, an electric field may be applied to the sample matrix, the electric field being configured so as to cause movement of the analyte towards the capture species. Such a method can speed up measurement time by causing movement of the species in the sample to migrate to the sensing element at a movement speed which is greater than diffusion. This can reduce the time of or reduce the need for an incubation period. This may also be used as a further filter of the sample, since different species will move at different rates and therefore may be selectively driven to (or beyond) the sensing element, also speeding up measurement time and accuracy.

The through holes of the sensing layer and electric field also provide additional synergies. The through holes provide electric field confinement which increases the strength of the electric field within and adjacent the through holes. This increases the ability of the analyte to interact with the through holes and allows for low voltage sensor systems to create higher strength electric fields than would otherwise be achieved without these types of structure in the sensing layer.

System

The system may be configured to perform any of the method steps disclosed herein. Moreover, any of the embodiments set out herein with respect to the method apply equally to the system, and any of the embodiments set out herein with respect to the system apply equally to the method.

In one embodiment, the system may further comprise a signal processing unit configured to process measurement signals received from the sensor assembly; and the property determination unit may receive processed signals and determine the property based on the processed signals. The property determination unit may, in certain embodiments, be configured to determine the property based on (at least) the absolute change in measurement signal and/or the rate of change of the signals.

The control unit, property determination unit and/or signal processing unit may each (individually or combined) be a processor or controller. The control unit may incorporate the property determination unit and/or the signal processing unit or may be in addition to one or both of these. The control unit, signal processing unit, and the property determination unit may be implemented in any suitable manner, with software and/or hardware, to perform the various functions required. One or all of the units may, for example, employ one or more microprocessors programmed using software (for example, microcode) to perform the required functions. Examples of processor components that may be employed in various embodiments include, but are not limited to, conventional microprocessors, application specific integrated circuits (ASICs), and field-programmable gate arrays (FPGAs).

In various implementations, the control unit, the signal processing unit, and/or property determination unit may be associated with one or more non-transitory storage media such as volatile and non-volatile computer memory such as RAM, PROM, EPROM, and EEPROM. The non-transitory storage media may be encoded with one or more programs that, when executed on one or more processors and/or controllers, perform the required functions. Various storage media may be fixed within a processor or controller or may be transportable, such that the one or more programs stored thereon can be loaded into the signal processing unit, property determination unit and/or control unit.

In certain embodiments, the control unit may be configured to alter at least one parameter of the electric field during the step of removing at least a portion of the non-specifically-bound species from the sensing element based on the sample baseline measurement. This can be carried out according to the method set out herein.

In one aspect, there is provided a computer program comprising computer program code which is configured, when said computer program is run on one or more physical computing devices, to cause said one or more physical computing devices to implement the methods disclosed herein.

In one aspect, there is provided one or more non-transitory computer readable media having a computer program stored thereon, the computer program comprising computer program code which is configured, when said computer program is run on one or more physical computing devices, to cause said one or more physical computing devices to implement the method disclosed herein.

Method

As noted above, the method may comprise carrying out any of the steps carried out in respect of the sensor assembly and system disclosed herein. For example, the method may additionally comprise carrying out any of the steps the control unit, signal processing unit and/or property determination unit are configured to carry out.

In one aspect, a method for determining a property of an analyte in a sample comprises providing a sensor assembly, the sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface, wherein the sensing element is arranged in the fluid chamber such that sample can reside above the upper surface, reside below the lower surface and pass through the through holes in the sensing layer; and capture species configured to specifically bind with analyte provided on the sensing layer, wherein the capture species are located adjacent and/or in the through holes such that analyte bound to the capture species can interact with the through holes of the sensing layer so as to alter an impedimetric property of the sensing layer. The method further comprises providing the sample to the sensing element, wherein at least a portion of analyte in the sample binds to the capture species to form specifically-bound analyte; obtaining a measurement signal indicative of the impedimetric property of the sensing layer from the sensing element; and determining the property of the analyte based on the impedimetric property of the sensing layer indicated by the measurement signal.

In one embodiment, the method further comprises manipulating at least a portion of the specifically-bound analyte by applying a force to the sample sufficient to move specifically-bound analyte on the sensing element, wherein determining the property of the analyte in the sample is based on the measurement signal during and/or after the step of manipulating specifically-bound analyte.

In one embodiment, the method further comprises detaching at least a portion of the specifically-bound analyte by applying a force to the sample sufficient to detach specifically-bound analyte from the sensing element, wherein determining the property of the analyte in the sample is based on the measurement signal during and/or after the step of detaching the specifically-bound analyte.

In one embodiment, the step of providing the sample to the sensing element comprises applying an electric field to the sample on the sensing element, the electric field being configured so as to cause movement of the analyte towards the capture species.

In one embodiment, the force is provided by at least one of an electric field or a magnetic field.

In one embodiment, the sample comprises the analyte, non-analyte species and a sample matrix in which the analyte and non-analyte species are contained; and during the step of providing the sample to the sensing element at least a portion of analyte and/or non-analyte species in the sample non-specifically bind to the sensing element; the method further comprises removing at least a portion of the non-specifically-bound analyte and/or non-analyte species from the sensing element by applying an electric field to the sample matrix, the electric field configured to remove non-specifically-bound analyte and/or non-analyte species from at least a portion of the sensing element but having a strength less than that required to detach specifically-bound analyte from the sensing element.

In some embodiments, the method further comprises modulation of the measurement signal in time, frequency, current, and/or voltage domains. This will generate more signal on biorecognition to differentiate between specific and non-specific binding.

Specific Uses

In embodiments of the methods, sensor assembly and systems disclosed herein, these can be used to distinguish between minor mutations or modifications of analyte species, such as biomolecules or structures. Specifically, there is a need to be able to distinguish between the types of modifications or differences which occur, either through modification or during synthesis, in species such as DNA or proteins. Traditional methods such as chromatography or mass spectroscopy focus on the mass and/or size of these species, making it different to distinguish where structural differences exist but where the mass or size differences are too small to reliably determine or filter out mismatches. This is particularly the case for biomolecules, where the relative size or mass of the total molecule is typically large as compared to the difference in physical size or mass resulting from the mismatch.

For example, in one embodiment of the methods, sensor assembly and systems disclosed herein, these can be used to identify DNA or RNA mismatches or differentiate/separate DNA or RNA based on the degree of differentiation. DNA or RNA mismatches can occur during the synthesis (e.g. by replication) of DNA or RNA where there is a mismatch between the original DNA or RNA and the synthesized version. This can be as a result of inserting an incorrect nt (or base pair) or deletion of a base pair, for example. Another example is a modification, for example as a result of glycosylation of the DNA/RNA. Such mismatches will alter the binding affinity between the capture species and the DNA or RNA (i.e. analyte) of interest due to a mismatch between the capture species and the analyte. A complete match will have a first binding affinity, some minor mismatch may still bind but with a lower affinity, and more mismatched bases will lead to no selective binding of the capture species and the DNA/RNA. Distinction between the binding components can be determined by the binding affinity, and specifically by the force required to remove the DNA/RNA being analyzed.

For example, in one embodiment, the method may comprise applying a force of a first magnitude which is less than the force used in the detachment step (but may be greater than that in the removal step, since the binding affinity will be higher than for non-specifically bound species). This can be less than the force required to overcome the binding affinity between a non-mismatched (i.e. perfect matched DNA or RNA structure), or in some embodiments a mismatched DNA or RNA structure which is a sufficiently close match (e.g. <1% of bases mismatched, or less than 0.1% of bases) such that only components which are (i) either not specifically bound or (ii) are bound to the capture species but with a binding affinity which is lower than the desired DNA or RNA structure will be removed. This allows the method to strip away any mismatched DNA or RNA. Any DNA or RNA having the desired structure will remain bound to the capture species and be retained on the sensor assembly. Subsequent analysis can be used to determine the amount of DNA/RNA which remains, for example measurement, manipulation and/or detachment steps.

Additionally or alternatively, this can be used as a filter. Specifically, the non-desired species can be removed from the system after it has been detached from the capture species. Subsequently, the disclosed detachment steps can be used to detach the desired DNA or RNA from the sensor assembly and retained as a separate component.

In one other embodiment, and using the same techniques and steps as set out above for the DNA/RNA mismatch, another embodiment includes determining changes in a protein, for example due to glycosylation, or filtering out glycosylated and non-glycosylated proteins.

Specific Embodiments

FIGS. 1 and 2A to 2E schematically depict a system 100 for determining a property of an analyte 2 in a sample, the sample comprising the analyte 2, non-analyte species 4 and a sample matrix in which the analyte 2 and non-analyte species 4 are contained. FIG. 1 provides a schematic plan view of the system 100 and FIGS. 2A to 2E provide a schematic cross-sectional view of the system 100 along line A shown in FIG. 1. It will be appreciated that the schematic drawings are provided to exemplify the concepts provided herein and the components, such as the through holes and capture species, are not intended to be to scale.

The system 100 comprises a sensor assembly 105 comprising a sensing element 110, the sensing element 110 comprising a sensing layer 115 having a plurality of through holes 130 extending from an upper surface to a lower surface. The sensing layer 115 is suspended in a chamber such that fluid resides on both sides of the sensing layer 115 and with the through holes 130 providing for passage of fluid from the region above the sensing layer 115 to below the sensing layer 115. The sensing layer 115 is functionalised with capture species 120 configured to specifically bind with the analyte provided on the upper surface adjacent the through holes 130.

The sensing element 110 also comprises an interdigitated electrode (IDE) 116 formed from a first electrode 117 and a second electrode 119 arranged in an interdigitated configuration, as visible from the plan view of FIG. 1. Specifically, the first electrode 117 comprises a first connector 117a which extends along one side of the sensing layer 115 and from which plural first extension portions 117b extend perpendicularly. These first extension portions 117b are spaced apart from one another. The second electrode 119 comprises a second connector 119a which extends along the opposite side of the sensing layer 115 to the first connector 117a and plural second extension portions 119b extend perpendicularly from the second connector 119a towards the first connector 117a. The second extension portions 119b are also spaced apart from one another but are staggered as compared to the first extension portions 117b. In this way, the second extension portions 119b are received between the first extension portions 117b to form the IDE 116. This can be referred to as an interdigitated comb configuration.

The sensing layer 115 is arranged so that the majority of the sensing layer is located between the first extension portions 117b and second extension portions 119b of the first electrode 117 and second electrode 119, respectively. The IDE 116 is therefore provided with the through holes 130 of the sensing layer 115 between the interdigitated portions of the first electrode 117 and second electrode 119. This allows the IDE 116 to detect changes in the impedimetric properties of the sensing layer 115 caused by interaction of species with (such as intrusion into) the through holes. Moreover, the use of the IDE 116 in this way enables the miniaturisation of the system by eliminating the need for a reference electrode, without sacrificing or reducing the accuracy of the system, enabling use in point-of-care situations.

As such, the sensing layer 115, capture species 120 and IDE 116 are selected and configured so that the sensing element 110 can provide a measurement signal indicative of the interaction of the sample with the sensing element 110.

The system 100 in the form set out above can be used to advantageously determine the property of the analyte 2, but may further comprise additional components to assist this measurement and/or improve the accuracy.

In this embodiment, the system 100 further comprises a sample manipulation device 140 which is for manipulating analyte 2 and/or non-analyte species 4 in the sample matrix (e.g. on the sensing element 110). The sample manipulation device 140 comprises a first manipulation electrode 144 provided above the sensing layer 115 and a second manipulation electrode 142 electrically connected to the first manipulation electrode 144 and located below the sensing layer 115. These are separate to the IDE 116. The first manipulation electrode 144 and second manipulation electrode 142 are configured to apply an electric field through the sample matrix and about the sensing element 110 so that movement of the analyte 2 and non-analyte species 4 within the sample matrix can be controlled by the electric field generated therebetween. Specifically, the arrangement of the first and second manipulation electrodes 144, 142 above and below the sensing layer 115 permits movement substantially perpendicular to the upper and lower surfaces of the sensing layer 115 and in a direction through the through holes 130. This enables movement from one side of the sensing layer 115 to the other side, for example.

The system 100 further comprises a control unit 150 which is a processor configured to operate the sample manipulation device 140. Specifically, the control unit 150 is configured to operate the sample manipulation device 140 to generate the electric field using the first and second manipulation electrodes 144, 142, as will be explained in more detail below. In this embodiment, the control unit 150 also comprises a property determination unit configured to determine the property of the analyte. This determination is based on the measurement signal obtained from the sensing element 110 (specifically, by addressing the IDE 116), as detailed below.

Figures 2B, 2C:
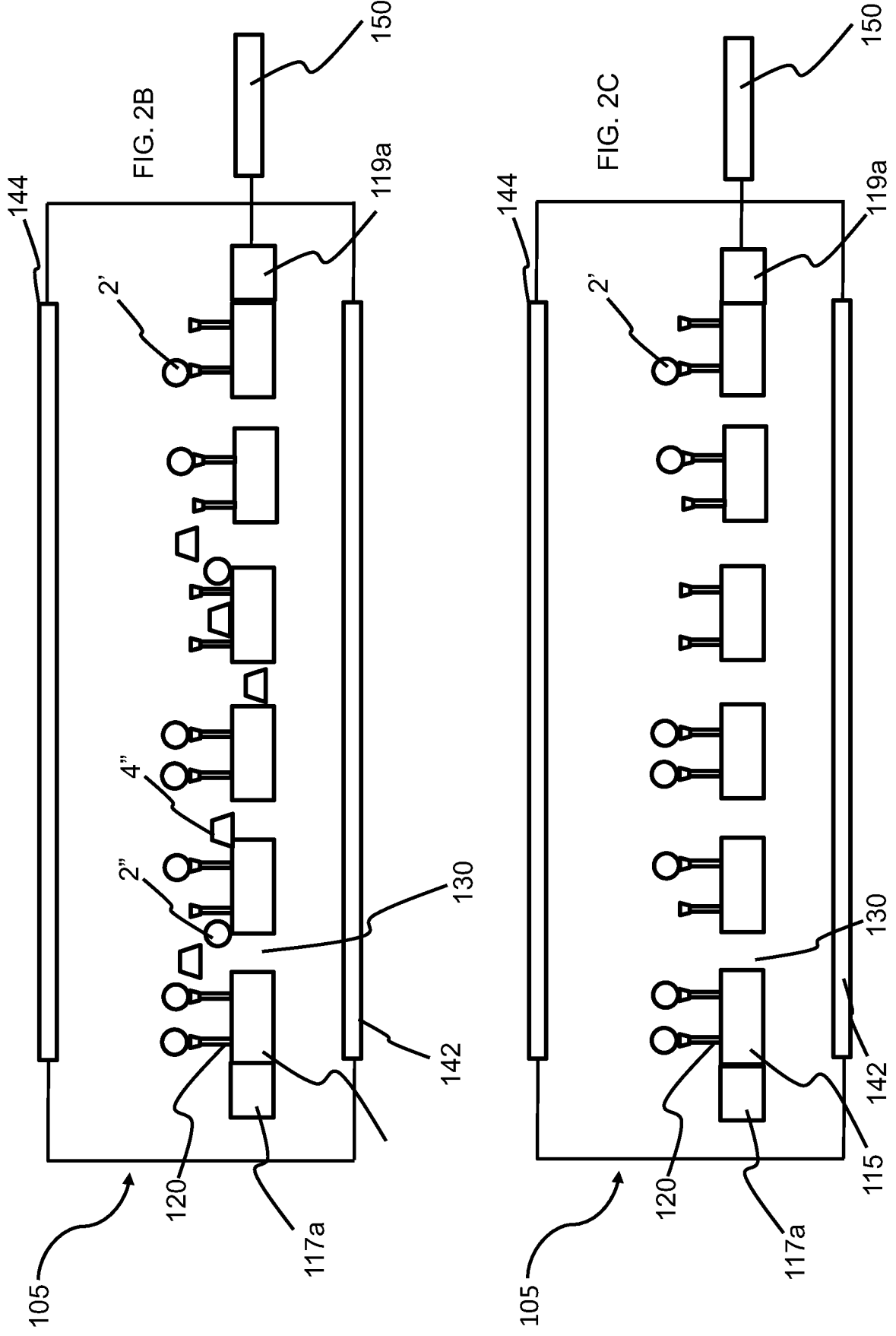

In use, analyte 2 provided to the system 100 will specifically bind to the capture species to form specifically-bound analyte 2', as depicted in FIG. 2B. Additionally, some analyte may non-specifically bind to the surface of the sensing layer 115 to form non-specifically-bound analyte 2". Non-analyte species 4 may also non-specifically bind to sensing layer 115 to form further non-specifically-bound non-analyte species 4". Although the main interaction of interest is that between the capture species 120 and the analyte 2, which will contribute to a response in the measurement signal, the non-specific binding of the species will also contribute to the signal. This interaction can reduce the sensitivity of the measurement and slow down the measurement process. In some cases, non-specific binding can lead to sensor failure.

Figure 3:
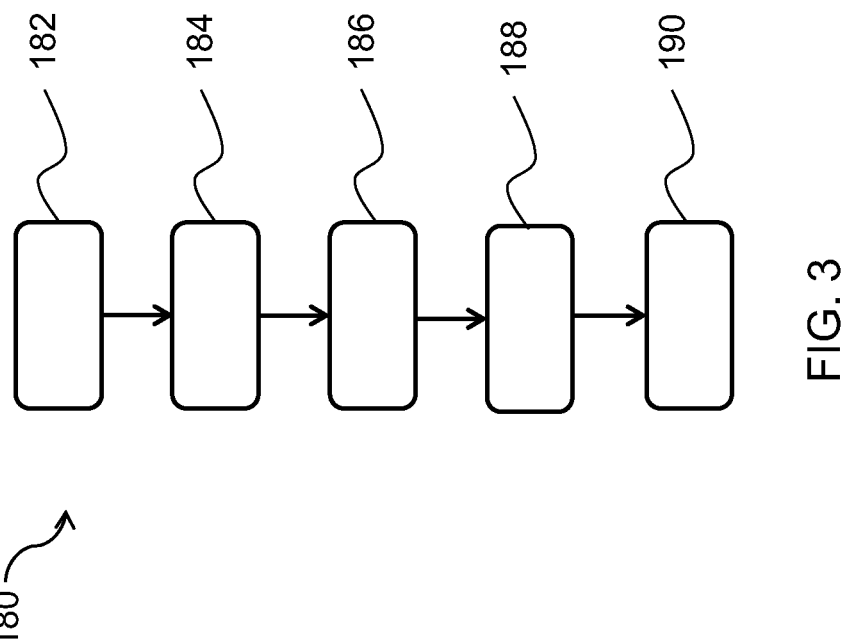
FIG. 3 provides a block diagram of a method according to an embodiment.

A method 180 of determining a property of an analyte in a sample, using the system 100, is depicted in FIG. 3 and set out below with reference to FIGS. 2A to 2C. The method 180 comprises providing 182 the sensor assembly 105 followed by providing 184 the sample to the sensing element 110. As shown in FIG. 2B, at least a portion of analyte 2 and non-analyte species 4 in the sample non-specifically bind to the sensing layer 115 to form non-specifically-bound analyte 2" and non-specifically-bound non-analyte species 4" and least a portion of analyte 2 specifically-binds to the sensing layer 115 to form specifically-bound analyte 2'.

The method 180 further comprises obtaining a sample baseline measurement 186 based on the measurement signal. The measurement signal can be taken at the point in time depicted by FIG. 2B and therefore is based on the contribution to the signal provided by specifically-bound analyte 2' and the non-specifically-bound species (analyte 2" and non-analyte 4"). This measurement signal is obtained and processed by the control unit 150.

The method 180 further comprises removing at least a portion of the non-specifically-bound analyte and/or non-analyte species from the sensing element by applying an electric field to the sample matrix ("removal step" 188). The electric field in system 100 is formed using the sample manipulation device 140 under the action of the control unit 150.

This removal step 188 causes removal of non-specifically-bound analyte and/or non-analyte species from at least a portion of the sensing element by providing a force which acts on the species driving them away from one of the first and second manipulation electrodes 144, 142 and towards the other. In one implementation depicted in FIG. 2C, the electric field is configured to move the species towards the second manipulation electrode 142, and as such the species move from the region above the upper surface of the sensing layer 115 to the region below the lower surface of the sensing layer 115. This can also lead to passage through the through holes 130. During this step, the electric field is applied with a strength that is less than that required to detach specifically-bound analyte 2' from the sensing layer

115. This can be determined based on strength of the interaction (affinity) between the capture species 120 and the analyte 2.

The removal step 188 accordingly strips away the non-specifically-bound species 2", 4" from the sensing layer 115 leaving behind specifically-bound analyte 2' on the surface. In this way, the contribution of the non-specifically-bound species to the measurement signal is eliminated or at least reduced, thereby improving the accuracy of the measurement overall.

The method can therefore further comprise determining the property of the analyte in the sample 190 based on the measurement signal after the removal step 188. The measurement signal is indicative of an impedimetric property of the sensing layer 115. For example, in one embodiment of the method, prior to interaction of the sensing layer 115 with the sample, the permittivity of the sensing layer is determined by the sensing layer 115 and any fluid within the through holes 130. Typically this will be a liquid, such as an aqueous solution, which typically have a permittivity of ~80. However, once analyte 2 is bound to the capture species 120 and can interact with the through holes 130, such as enter and traverse through, the analyte 2 (and potentially the capture species 120) will contribute to the impedimetric property of the sensing layer 115. The permittivity of analyte species such as biomolecules tends to be over an order of magnitude less (e.g. 3-5) such that this results in a measurement signal that can be detected. This can be detected by addressing the IDE 116 with an AC across a particular frequency range, for example.

In such a system 100 and method 180, determination of the sample baseline measurement 186 can be particularly useful. The measurement itself can be used to provide information on non-specific binding in the system, for example the speed of the incubation process and the degree of binding. Moreover, it can further be used to improve the accuracy of subsequent measurement processes.

For example, in some embodiments of the method 180, the sample baseline measurement is used to determine at least one parameter of the removal step 188. This can be prior to the beginning of the removal step 188 or during the removal step 188. For example, the level of the sample baseline measurement may determine at least one of the duration of the removal step or the parameters of the electric field, such as at least one of the duration of the application of the electric field to the sample matrix, the strength of the electric field, or the number of repetitions of the application of the electric field. This may be a feedback loop whereby the control unit 150 may further determine an adjustment factor based on the measurement signal during or after application of the electric field and during the removal step 188 but after the initial sample baseline measurement. This essentially takes an intermediate measurement during the removal step 188 and the adjustment parameter may be used to change one of the parameters of the removal step 188. This can be, for example, an increase in the duration and/or intensity if the response to the removal step 188 is having little or no effect or a decrease in the duration and/or intensity if it is thought that the removal step 188 has finished.

One useful metric for monitoring the removal step 188, for example particularly where the magnitude of non-specific binding is not known, can be rate of change. The adjustment factor can therefore be based on the rate of change in the measurement signal during the removal step 188.

In other embodiments, which provide an additional or alternative use of the sample baseline measurement, the sample baseline measurement can be used to compensate measurement signals in future measurements and avoid the need for a repeated removal step 188. For example, a signal compensation factor can be determined by the control unit 150, which can be derived from determining the amount of the measurement signal attributable to non-specific binding, and the subsequent determination of the future measurement can use the measurement signal for the second sample and the signal compensation factor.

Figure 4:
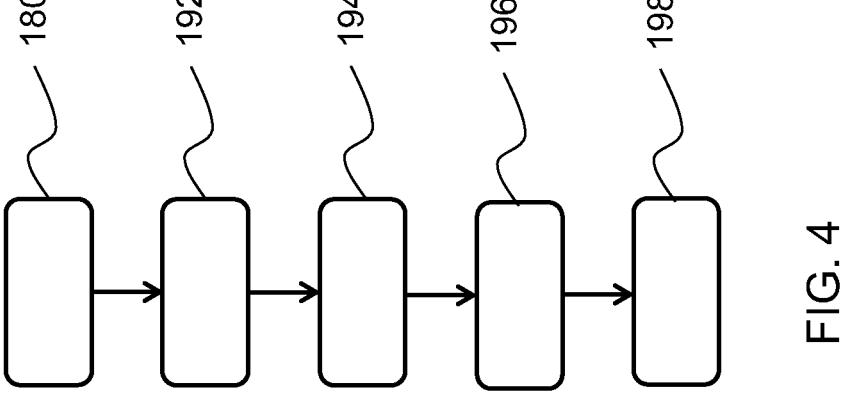
FIG. 4 provides a block diagram of a method according to an embodiment.

FIG. 4. depicts additional method steps 192-196 which can be carried out in addition to the method depicted in FIG. 3 and in conjunction with system 100. The additional steps depicted therein can follow on from method 180, as shown in FIG. 3 and depicted in FIGS. 2D and 2E.

Figures 2D, 2E:
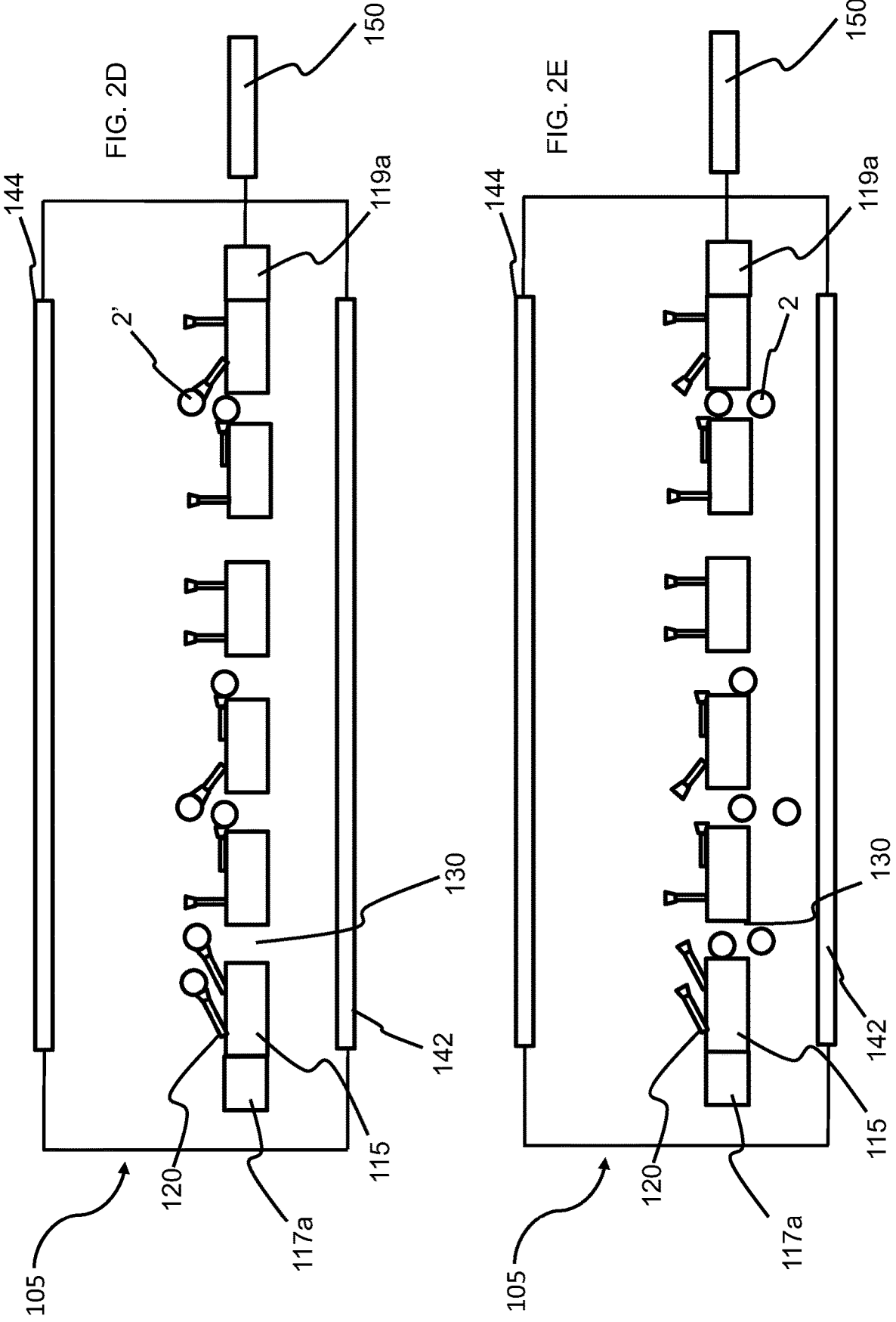

In this embodiment, the method further comprises manipulating at least a portion of the specifically-bound analyte ("manipulation step" 192) after the step of removing at least a portion of the non-specifically-bound analyte and/or non-analyte components from the sensing element. In this embodiment, the electric field generated between the first and second manipulation electrodes 144, 142 is actuated with a higher intensity than in the removal step 188 so that there is movement of the specifically-bound analyte on the sensing layer 115. With the configuration of the first and second manipulation electrodes 144, 142 above and below the sensing layer 115 and the through holes 130 located adjacent the capture species 120, this movement can move the specifically-bound analyte 2' into the through holes 130 and, depending on the length and position of the capture species, in some embodiments through the through holes 130, as depicted in FIG. 2D.

This manipulation step 192 will generate specific responses and change in the response of the sensing element (i.e. the measurement signal). This can be monitored over time to build up an interaction picture and provide further information on the analyte. For example, the kinetics of movement or the specific interactions could be used as a fingerprint indicative of the presence of the analyte and a quantity of the analyte. For example, the response may vary based on the speed of movement or interaction with the through holes 130 based on the size and nature of the analyte 2. Accordingly, the method further comprises determining the property of the analyte in the sample 194 based on the measurement signal during and/or after the manipulation step 192.

In some embodiments, determining the property of the analyte in the sample 194 is based on the rate of change in the measurement signal during the step of manipulating the specifically-bound analyte. This can help to build up the picture or fingerprint providing a higher degree of accuracy and certainty. Unlike typical electrochemical measurements, the rate of change is particularly beneficial in these methods given the manipulation of the analyte and therefore the varying response.

The method in this embodiment further comprises detaching at least a portion of the specifically-bound analyte (detachment step 196) after the step of removing at least a portion of the non-specifically-bound analyte and/or non-analyte components from the sensing element. Detaching specifically-bound analyte comprises applying a force to the sample matrix sufficient to detach specifically-bound analyte from the sensing element, which in this is achieved by further increasing the strength of the electric field provided by the sample manipulation device 140 to a strength that overcomes the affinity between the capture species 120 and the analyte 2.

In FIG. 2E, the result of the step of detaching the analyte (detachment step 196) can be seen. Due to the specific electric field applied, movement of the analyte 2 from the first manipulation electrode 144 to the second manipulation electrode 142 occurs such that the analyte passes through the through holes 130 and to the underside of the sensing layer 115.

The method accordingly further comprises determining the property of the analyte in the sample 198 based on the measurement signal during and/or after the step of detaching the specifically-bound analyte 2'.

As with the manipulation step 192, the detachment step 196 may be a simple linear application of the force (i.e. the electric field in this embodiment) or it may comprise different applications of force to obtain further information about the response of the sensor assembly 105.

Figures 5A, 5B, 5C, 5D, 6:
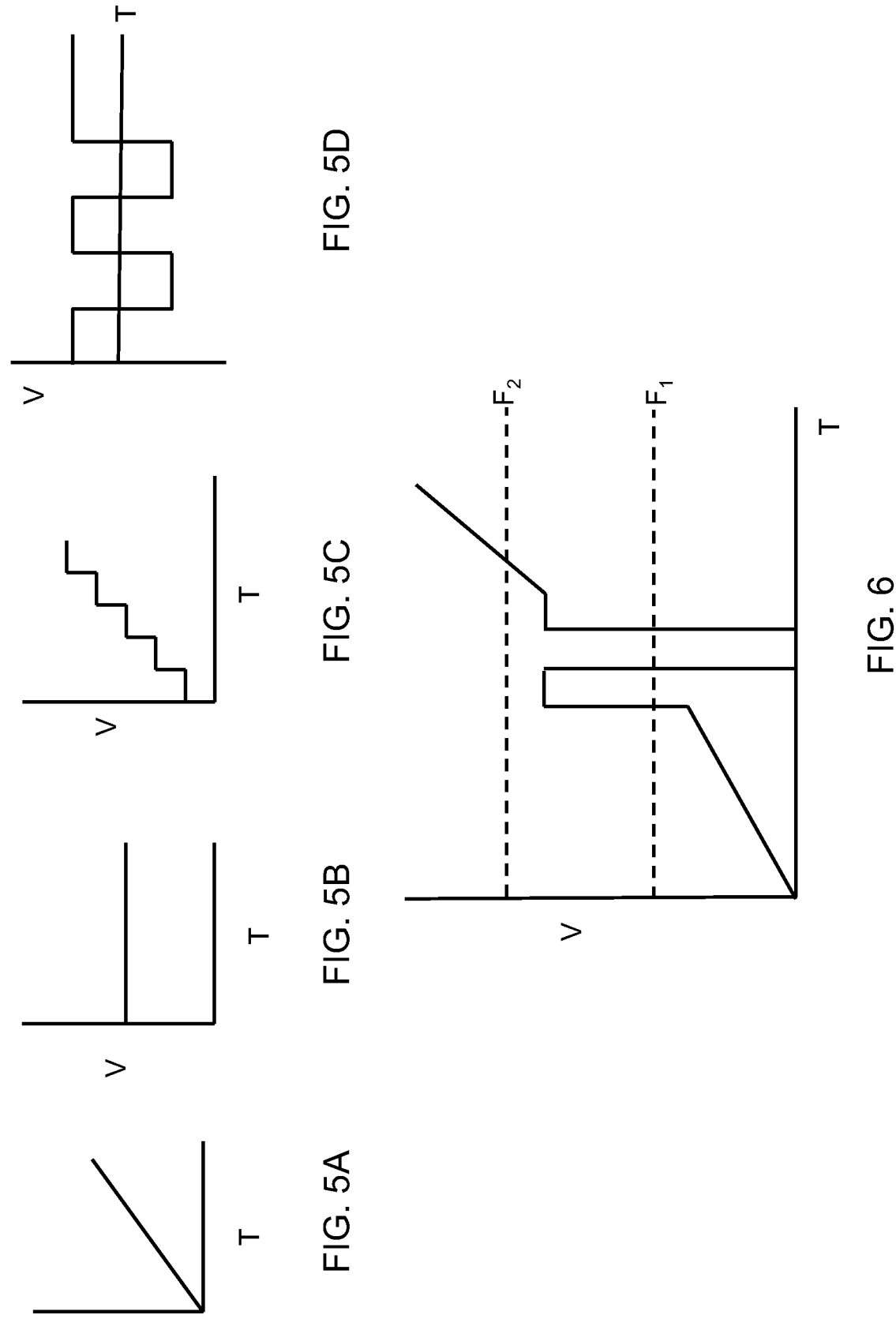
FIGS. 5A to 5D provide example applied voltage schemes for a removal step according to an embodiment.
FIG. 6 provides an example applied voltage scheme according to an embodiment.

FIGS. 5A to 5D depict example parameters for applying the electric field in the removal step 188, with voltage (V) plotted against time (T). The method 180 set above can different parameters during the removal step 188, and additionally any manipulation step 192 and detachment step 196. FIG. 4A depicts a linear ramp over time from no electric field to a maximum (which for the removal step is less than that which would cause detachment of specifically-bound analyte 2'). This can lead to staggered removal of the non-specifically-bound species. FIG. 5B depicts a hold at a single intensity. FIG. 5C depicts a series of increasing steps. This too may lead to staggered removal of the non-specifically-bound species and may provide useful information about particular non-specifically-bound species where the relative non-specifically-bound affinities are known, for example. FIG. 5D depicts an alternating application of the electric field where the polarity is switched. This can be used to drive the non-specifically-bound species back and forth through the through holes 130, for example, and in and out of interaction with the sensing element 110 thereby building up a picture. The final application of the electric field may comprise a hold at one intensity so as to remove the non-specifically-bound species from the sensing element 110.

Although FIGS. 5A to 5D depict the profiles that could be used for the removal step 188, it will be appreciated that the same profiles could be used for the manipulation step 192 and detachment step 196 with modification for the maximum or magnitude of the force applied (e.g. the electric field strength).

FIG. 6 depicts an example for applying the electric field in the method 180 and subsequent manipulation step 192 and detachment step 196, with voltage (V) plotted against time (T). This depicts a first linear ramp for a period of time in the removal step 188 where the non-specifically-bound components are removed. The voltage is then increase above $F_1$, with $F_1$ corresponding to the force at which there is substantial movement of the specifically-bound analyte 2' on the sensing layer 115 (as depicted in FIG. 2D), where it is held for a period of time before the electric field is turned off. This allows the capture species 120 and specifically-bound analyte 2' to relax, before the electric field is reapplied for a period of time. There is a final ramp to a voltage which provides a force above $F_2$, with $F_2$ corresponding to the force required to overcome the binding between capture species 120 and analyte 2.

Although the embodiment of FIG. 6 has been depicted with reference to use of the same electric field throughout each of the removal step 188, the manipulation step 192 and the detachment step 196, it will be appreciated that these may be applied using different manipulation means. For example, the manipulation step 192 and the detachment step 196 may be carried out using a separate manipulation unit, for example a magnetic field generator or a separate electrode array.

Figure 7:
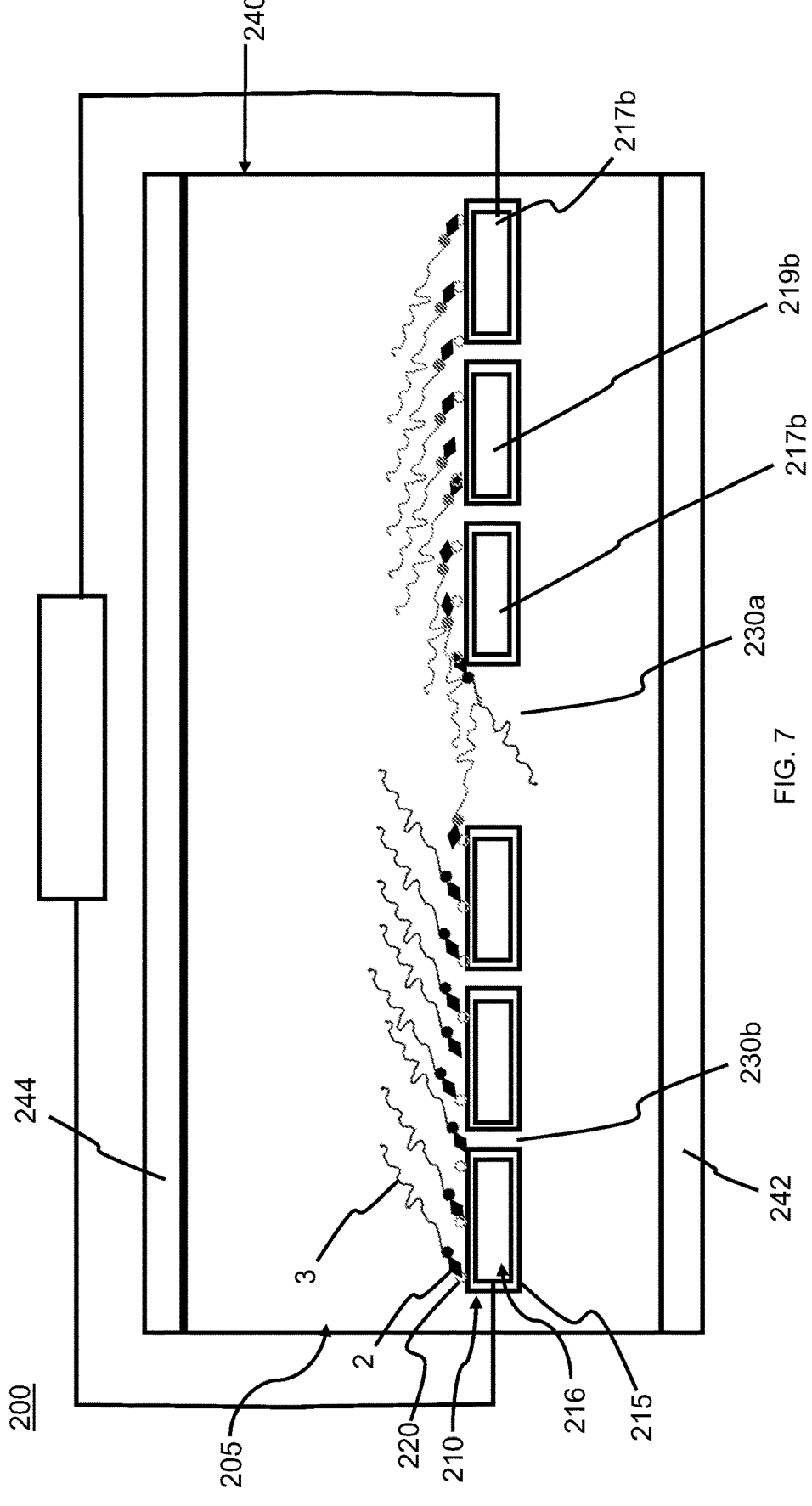
FIG. 7 provides a schematic cross-sectional view of a system according to an embodiment.

FIG. 7 schematically depicts a system 200 for determining a property of an analyte 1 in a sample in cross-section.

The system 200 is similar to the system 100 of FIGS. 1 and 2A to 2E in that it comprises a sensor assembly 205 comprising a sensing element 210, the sensing element 210 comprising a sensing layer 215 having a plurality of through holes 230a, 230b extending from an upper surface to a lower surface of the sensing layer 215. The sensing layer 215 is suspended in a chamber such that fluid resides on both sides of the sensing layer 215 and with the through holes 230a, 230b providing for passage of fluid from the region above the sensing layer 215 to below the sensing layer 215. Sensing layer 215 is functionalised with capture species 220 configured to specifically bind with the analyte 2 provided on the upper surface adjacent the through holes 230a, 230b.

In this embodiment, the sensing element 210 also comprises an interdigitated electrode (IDE) 216 formed from a first electrode and a second electrode arranged in an interdigitated configuration. Specifically, the first electrode comprises a first connector which extends along one side of the sensing layer 215 and from which plural first extension portions 217b extend perpendicularly. These first extension portions 217b are spaced apart from one another. The second electrode comprises a second connector which extends along the opposite side of the sensing layer 215 to the second connector 219a and plural second extension portions 219b extend perpendicularly from the second connector 219a towards the first connector. The second extension portions 219b are also spaced apart from one another but are staggered as compared to the first extension portions 217b. In this way, the second extension portions 219b are received between the first extension portions 217b to form the IDE 216. This can be referred to as an interdigitated comb configuration. In FIG. 7, the cross-section is taken to show a plane extending perpendicularly through the first extension portions 217b and second extension portions 219b. In this embodiment, the IDE 116 is embedded in the sensing layer 215 such that the sensing layer 215 surrounds each of the first extension portions 217b and second extension portions 219b. This avoids direct interaction of the sample with the IDE 116, helping to reduce interference in the measurement signal. Moreover, this also provides sensing layer 215, and accordingly through holes 230a, 230b, between the first extension portions 217b and second extension portions 219b.

In this embodiment, however, the sensing layer 215 comprises through holes 230a, 230b of different widths. Specifically, first through holes 230a of a first width and second through holes 230b of a second, larger width. The different through holes will have different functions and have different interactions with species in the sample, such as analyte 2. For example, first through holes 230a may be used as flow through holes for removal of non-analyte portions, whereas the analyte 2 may only be able to interact with the larger second through holes 230b.

In this embodiment, the system 200 further comprises a sample manipulation device 240 which is for manipulating analyte 2 in the sample matrix (e.g. on the sensing element 210). As with the system 100 of FIGS. 1 and 2A to 2E, the sample manipulation device 240 of this embodiment comprises a first manipulation electrode 244 provided above the sensing layer 215 and a second manipulation electrode 242 electrically connected to the first manipulation electrode 244 and located below the sensing layer 215. These are separate to the IDE 216. The first manipulation electrode 244 and second manipulation electrode 242 are configured to apply an electric field through the sample matrix and about the sensing element 210 so that movement of the analyte 2 and any non-analyte species within the sample matrix can be controlled by the electric field generated therebetween.

One specific configuration in which the systems of the present invention is in a sandwich assay. In the context of the system 200 of FIG. 7, the assay comprises providing the capture species 220 on the surface of the sensing layer 215 and additionally providing a detection species 3 which binds to the analyte 2. Examples include a sandwich ELISA assay, with the capture species 220 being a capture antibody, the detection species 3 being a detection antibody which may comprise double stranded DNA provided thereon. The DNA may be bound to the detection antibody via a linker, such as streptavidin and biotin.

As can be seen schematically in FIG. 7, the detection species 3 may provide the primary interaction with the through holes 230b which results in changes in the measurement signal, with the detection species being capable of being used in numerous assays providing a known response (for example, as compared to the analyte). As the detection species 3 is driven into the through holes 230b (depicted in FIG. 7), this can cause a spike or significant change in the measurement signal.

FIGS. 8A to 8D provide schematic cross-section views of a sensing layer 315 with a through hole 330 provided therein and the use of an amplification bead 3'. FIG. 8E schematically depicts a graph showing an example signal(S) corresponding to the configurations shown in FIGS. 8A to 8D, plotted against time (T).

Specifically, the sensing layer 315 is provided with a capture species 320 to which an analyte 2 has bound. The system has also been provided with an amplification bead 3' which is attached to the analyte 2, in a similar manner to a sandwich assay. In this embodiment, the amplification bead 3' is a magnetic metallic bead and can be manipulated using a magnetic field (not shown) and which, together with the analyte 2, will have an effect on the impedimetric property of the sensing layer 315. FIG. 8A. depicts an initial configuration in which there is no magnetic field applied and the signal is at a baseline between $T_0$ and $T_1$. As the magnetic field is applied, amplification bead 3' is driven towards the sensing layer 315 (see FIG. 8B) but does not yet enter the through hole 330. This causes a change in signal between $T_1$ and $T_2$. as depicted in FIG. 8E. As the magnetic field is further applied, amplification bead 3' is driven through the through hole 330. FIG. 8C depicts the amplification bead within the through hole 330 which causes a large change in the impedimetric property of the sensing layer 315. This in turn causes a large change in signal (e.g. between $T_2$ and $T_3$). Finally, as the amplification bead 3' exits the through hole 330 on the other side of the through hole 330, the signal levels out with a new baseline (corresponding to the signal with the analyte 2 through the through hole 330). The rate of change and difference in signals before and after the manipulation process can all provide data used to confirm the presence and amount of an analyte.

FIG. 9 schematically depicts a cross-section through a system 400 comprising a sensor assembly 405. The sensor assembly 405 comprises a sensing element 410, the sensing element 410 comprising a sensing layer 415 formed of a passivation layer 415a providing the upper surface, an IDE 416 provided beneath the passivation layer 415a and a base sensing layer 415b provided beneath the IDE 416. The IDE 416 is accordingly embedded within sensing layer 415. The sensing layer 415 also comprises a plurality of through holes 430 extending from an upper surface of the passivation layer 415a to the lower surface of the sensing layer 415b. In this embodiment, the sensing element 410 is suspended in a fluid chamber such that fluid resides on both sides of the sensing layer 415 by elevating the sensing element 410 on supports 406, in this case an oxide layer, which oxide layer is formed on silicon 407. Such sensor assemblies 405 can advantageously be formed using traditional CMOS manufacturing techniques.

The passivation layer 415a provides a surface which is more straightforward to functionalise and which can be used to limit interaction of the IDE 416 with species on the upper surface of the sensing layer 415, thereby focusing the signal changes on interaction with the through holes 430.

In one particular example based on the system 400, the system 400 can be used for performing an ELISA assay. The structure used in this particular example can comprise a silicon oxide supports 406 with a thickness of 1-2 μm. The passivation layer 415a is a 70 nm thick passivation layer. The IDE layer is a 50 nm thick titanium nitride (TiN) layer. The base sensing layer 415b is a 100 nm silicon nitride ($Si_3N_4$) dielectric layer. This creates a total depth of through hole 330 through the sensing layer 415 of 220 nm. The through holes 430 have a width of 400 nm. These dimensions provide a through hole which is responsive to ELISA structures. For example, the capture antibody can have a length of 10-15 nm and it may use a detection antibody provided with a double-stranded DNA of ~300 nm long, with a 2 nm diameter (900 base pairs).

It should be understood that the detailed description and specific examples, while indicating exemplary embodiments of the apparatus, systems and methods, are intended for purposes of illustration only and are not intended to limit the scope. These and other features, aspects, and advantages of the apparatus, systems and methods of the present invention can be better understood from the description, appended claims or aspects, and accompanying drawings. It should be understood that the Figures are merely schematic and are not drawn to scale. It should also be understood that the same reference numerals are used throughout the figures to indicate the same or similar parts.

Other variations to the disclosed embodiments can be understood and effected by those skilled in the art in practicing the disclosure, from a study of the drawings, the disclosure, and the appended aspects or claims. In the aspects or claims, the word "comprising" does not exclude other elements or steps, and the indefinite article "a" or "an" does not exclude a plurality. The mere fact that certain measures are recited in mutually different dependent aspects or claims does not indicate that a combination of these measures cannot be used to advantage. Any reference signs in the claims should not be construed as limiting the scope.

Aspects of the invention will now be disclosed:

Aspect 1. A system for determining a property of an analyte in a sample, the system comprising:

a sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface; and capture species configured to specifically bind with analyte provided on the sensing layer; and a property determination unit configured to determine the property of the analyte, wherein the sensing element is arranged in the fluid chamber such that sample can reside above the upper surface, reside below the lower surface and pass through the through holes in the sensing layer; wherein the sensing element provides a measurement signal indicative of an impedimetric property of the sensing layer; wherein the capture species are located adjacent and/or in the through holes such that analyte bound to the capture species can interact with the through holes of the sensing layer so as to alter the impedimetric property of the sensing layer; and wherein the property determination unit is configured to determine the property of the analyte based on the impedimetric property of the sensing layer indicated by the measurement signal.

Aspect 2. The system of aspect 1, wherein the sensing element comprises an interdigitated electrode (IDE) comprising a first electrode and a second electrode, the first and second electrodes arranged in an interdigitated configuration; and wherein at least a part of the sensing layer is arranged between the first electrode and second electrode of the IDE.

Aspect 3. The system of aspect 2, wherein the IDE is at least partially embedded within the sensing layer.

Aspect 4. The system of one of aspect 2 or aspect 3, wherein the first and second electrodes are spaced apart from one another by a spacing of from 10 nm to 10 μm.

Aspect 5. The system of any preceding aspect, wherein the capture species are configured such that an analyte bound to a capture species can be received within the through holes.

Aspect 6. The system of any preceding aspect, wherein the through holes have a largest diameter of less than or equal to 1000 nm.

Aspect 7. The system of any preceding aspect, wherein the sensing layer has a thickness of less than or equal to 1000 nm.

Aspect 8. The system of any preceding aspect, further comprising: a sample manipulation device for manipulating analyte and/or non-analyte species on the sensing element; and a control unit configured to operate the sample manipulation device; wherein the control unit is configured to operate the sample manipulation device so as to apply a force to the sample sufficient to move specifically-bound analyte on the sensing element; and wherein the property determination unit is configured to determine the property of the analyte in the sample based on the measurement signal during and/or after the control unit operates the sample manipulation device to move specifically-bound analyte.

Aspect 9. The system of aspect 8, wherein the sample manipulation device is configured to cause specifically-bound analyte to enter the through holes of the sensing layer.

Aspect 10. The system of one of aspect 8 or aspect 9, wherein the control unit is further configured to operate the sample manipulation device so as to apply a force to the sample sufficient to detach specifically-bound analyte on the sensing element and thereby detach at least a portion of specifically-bound analyte on the sensing element; and wherein the property determination unit is configured to determine the property of the analyte in the sample based on the measurement signal during and/or after the control unit operates the sample manipulation device to detach specifically-bound analyte.

Aspect 11. The system of any of aspects 8 to 10, wherein the sample manipulation device generates an electric field and/or a magnetic field to provide the force.

Aspect 12. The system of aspect 11, wherein the sample manipulation device comprises a plurality of electrodes configured to apply an electric field about the sensing element.

Aspect 13. The system of any of aspects 1 to 12, wherein the impedimetric property is selected from a dielectric property, resistance, capacitance, impedance, or conductance of the sensing layer, or a combination thereof.

Aspect 14. A system for determining a property of an analyte in a sample, the system comprising:

a sensor assembly comprising: a sensing element, the sensing element comprising: an interdigitated electrode (IDE) comprising a first electrode and a second electrode, the first and second electrodes arranged in an interdigitated configuration; a sensing layer arranged at least in part between the first electrode and second electrode of the IDE, the sensing layer comprising an upper surface and a lower surface and a plurality of through holes, each of the through holes extending from the upper surface to the lower surface; and capture species configured to specifically bind with the analyte provided on the sensing layer, wherein the capture species are located adjacent and/or in the through holes such that analyte bound to the capture species can interact with the through holes of the sensing layer; and wherein the sensing element provides a measurement signal indicative of the interaction of the sensing element with the analyte.

Aspect 15. The system of aspect 14, wherein the capture species are located adjacent and/or in the through holes such that analyte bound to the capture species can interact with the through holes of the sensing layer so as to alter the impedimetric property of the sensing layer; wherein the sensing element provides a measurement signal indicative of the impedimetric property of the sensing layer; and wherein the system further comprises a property determination unit configured to determine the property of the analyte based on the impedimetric property of the sensing layer indicated by the measurement signal.

Aspect 16. The system of aspect 15, wherein the impedimetric property is selected from a dielectric property, resistance, capacitance, impedance, or conductance of the sensing layer, or a combination thereof.

Aspect 17. A method for determining a property of an analyte in a sample, the method comprising: providing a sensor assembly, the sensor assembly comprising: a fluid chamber for receiving a sample; and a sensing element comprising: a sensing layer, the sensing layer comprising an upper surface and a lower surface and a plurality of through holes, each of the through holes extending from the upper surface to the lower surface, wherein the sensing element is arranged in the fluid chamber such that sample can reside above the upper surface, reside below the lower surface and pass through the through holes in the sensing layer; and capture species configured to specifically bind with analyte provided on the sensing layer, wherein the capture species are located adjacent and/or the through holes such that analyte bound to the capture species can interact with the through holes of the sensing layer so as to alter a impedimetric property of the sensing layer; providing a sample to the sensing element, wherein at least a portion of analyte in the sample binds to the capture species to form specifically-bound analyte; obtaining a measurement signal indicative of the impedimetric property of the sensing layer from the sensing element; and determining the property of the analyte based on the impedimetric property of the sensing layer indicated by the measurement signal.

Aspect 18. The method of aspect 17, further comprising manipulating at least a portion of the specifically-bound analyte by applying a force to the sample sufficient to move specifically-bound analyte on the sensing element, wherein determining the property of the analyte in the sample is based on the measurement signal during and/or after the step of manipulating specifically-bound analyte.

Aspect 19. The method one of aspect 17 or aspect 18, further comprising detaching at least a portion of the specifically-bound analyte by applying a force to the sample sufficient to detach specifically-bound analyte from the sensing element, wherein determining the property of the analyte in the sample is based on the measurement signal during and/or after the step of detaching the specifically-bound analyte.

Aspect 20. The method of any of aspects 17 to 19, wherein the step of providing the sample to the sensing element comprises applying an electric field to the sample on the sensing element, the electric field being configured so as to cause movement of the analyte towards the capture species.

Aspect 21. The method of any of aspects 18 to 20, wherein the force is provided by at least one of an electric field or a magnetic field.

Aspect 22. The method of any of aspects 17 to 21, wherein the sample comprises the analyte, non-analyte species and a sample matrix in which the analyte and non-analyte species are contained; wherein during the step of providing the sample to the sensing element at least a portion of analyte and/or non-analyte species in the sample non-specifically bind to the sensing element; and wherein the method further comprises removing at least a portion of the non-specifically-bound analyte and/or non-analyte species from the sensing element by applying an electric field to the sample matrix, the electric field configured to remove non-specifically-bound analyte and/or non-analyte species from at least a portion of the sensing element but having a strength less than that required to detach specifically-bound analyte from the sensing element.

Aspect 23. The method of any of aspects 17 to 22, wherein the impedimetric property is selected from a dielectric property, resistance, capacitance, impedance, or conductance of the sensing layer, or a combination thereof.

The invention claimed is:

1. A system for determining a property of an analyte in a sample, the system comprising:
  a sensor assembly comprising:
    a fluid chamber for receiving a sample; and
    a sensing element comprising:
      a sensing layer, the sensing layer comprising an upper surface and a lower surface and a plurality of through holes, each of the through holes extending from the upper surface to the lower surface; and
      capture species configured to specifically bind with analyte provided on the sensing layer; and
  a property determination unit configured to determine the property of the analyte,
  wherein the sensing element is arranged in the fluid chamber such that sample can reside above the upper surface, reside below the lower surface and pass through the through holes in the sensing layer;
  wherein the sensing element provides a measurement signal indicative of an impedimetric property of the sensing layer;
  wherein the capture species are located adjacent and/or in the through holes such that analyte bound to the capture species can interact with the through holes of the sensing layer so as to alter the impedimetric property of the sensing layer; and
  wherein the property determination unit is configured to determine the property of the analyte based on the impedimetric property of the sensing layer indicated by the measurement signal.

2. The system of claim 1,
  wherein the sensing element comprises an interdigitated electrode (IDE) comprising a first electrode and a second electrode, the first and second electrodes arranged in an interdigitated configuration; and
  wherein at least a part of the sensing layer is arranged between the first electrode and second electrode of the IDE.

3. The system of claim 2, wherein the IDE is at least partially embedded within the sensing layer.

4. The system of one of claim 2, wherein the first and second electrodes are spaced apart from one another by a spacing of from 10 nm to 10 $\mu$m.

5. The system of claim 1, wherein the capture species are configured such that an analyte bound to a capture species can be received within the through holes.

6. The system of claim 1, wherein the through holes have a largest diameter of less than or equal to 1000 nm.

7. The system of claim 1, wherein the sensing layer has a thickness of less than or equal to 1000 nm.

8. The system of claim 1, further comprising
  a sample manipulation device for manipulating analyte and/or non-analyte species on the sensing element; and
  a control unit configured to operate the sample manipulation device;
  wherein the control unit is configured to operate the sample manipulation device so as to apply a force to the sample sufficient to move specifically-bound analyte on the sensing element; and
  wherein the property determination unit is configured to determine the property of the analyte in the sample based on the measurement signal during and/or after the control unit operates the sample manipulation device to move specifically-bound analyte.

9. The system of claim 8, wherein the sample manipulation device is configured to cause specifically-bound analyte to enter the through holes of the sensing layer.

10. The system of one of claim 8, wherein the control unit is further configured to operate the sample manipulation device so as to apply a force to the sample sufficient to detach specifically-bound analyte on the sensing element and thereby detach at least a portion of specifically-bound analyte on the sensing element; and
  wherein the property determination unit is configured to determine the property of the analyte in the sample based on the measurement signal during and/or after the control unit operates the sample manipulation device to detach specifically-bound analyte.

11. The system of claim 8, wherein the sample manipulation device generates an electric field and/or a magnetic field to provide the force.

12. The system of claim 11, wherein the sample manipulation device comprises a plurality of electrodes configured to apply an electric field about the sensing element.

13. The system of claim 1, wherein the impedimetric property is selected from a dielectric property, resistance, capacitance, impedance, or conductance of the sensing layer, or a combination thereof.

14. A system for determining a property of an analyte in a sample, the system comprising:

A sensor assembly comprising:

A fluid chamber for receiving a sample;

A sensing element, the sensing element comprising:

An interdigitated electrode (IDE) comprising a first electrode and a second electrode, the first and second electrodes arranged in an interdigitated configuration;

A sensing layer arranged at least in part between the first electrode and the second electrode of the IDE, the sensing layer comprising an upper surface and a lower surface and a plurality of through holes, each of the through holes extending from the upper surface to the lower surface; and Capture species configured to specifically bind with the analyte provided on the sensing layer, Wherein the capture species are located adjacent and/or in the through holes such that analyte bound to the capture species can interact with the through holes of the sensing layer; and Wherein the sensing element provides a measurement signal indicative of the interaction of the sensing element with the analyte; and Wherein the sensing element is arranged in the fluid chamber such that sample can reside above the upper surface, reside below the lower surface and pass through the through holes in the sensing layer.

15. The system of claim 14, wherein the capture species are located adjacent and/or in the through holes such that analyte bound to the capture species can interact with the through holes of the sensing layer so as to alter the impedimetric property of the sensing layer;

wherein the sensing element provides a measurement signal indicative of the impedimetric property of the sensing layer; and wherein the system further comprises a property determination unit configured to determine the property of the analyte based on the impedimetric property of the sensing layer indicated by the measurement signal.

16. The system of claim 15, wherein the impedimetric property is selected from a dielectric property, resistance, capacitance, impedance, or conductance of the sensing layer, or a combination thereof.

17. A method for determining a property of an analyte in a sample, the method comprising:

providing a sensor assembly, the sensor assembly comprising:

a fluid chamber for receiving a sample; and a sensing element comprising:

a sensing layer, the sensing layer comprising an upper surface and a lower surface and a plurality of through holes, each of the through holes extending from the upper surface to the lower surface, wherein the sensing element is arranged in the fluid chamber such that sample can reside above the upper surface, reside below the lower surface and pass through the through holes in the sensing layer; and capture species configured to specifically bind with analyte provided on the sensing layer, wherein the capture species are located adjacent and/or the through holes such that analyte bound to the capture species can interact with the through holes of the sensing layer so as to alter an impedimetric property of the sensing layer;

providing a sample to the sensing element, wherein at least a portion of analyte in the sample binds to the capture species to form specifically-bound analyte;

obtaining a measurement signal indicative of the impedimetric property of the sensing layer from the sensing element; and determining the property of the analyte based on the impedimetric property of the sensing layer indicated by the measurement signal.

18. The method of claim 17, further comprising manipulating at least a portion of the specifically-bound analyte by applying a force to the sample sufficient to move specifically-bound analyte on the sensing element, wherein determining the property of the analyte in the sample is based on the measurement signal during and/or after the step of manipulating specifically-bound analyte.

19. The method one of claim 17, further comprising detaching at least a portion of the specifically-bound analyte by applying a force to the sample sufficient to detach specifically-bound analyte from the sensing element, wherein determining the property of the analyte in the sample is based on the measurement signal during and/or after the step of detaching the specifically-bound analyte.

20. The method of claim 17, wherein the step of providing the sample to the sensing element comprises applying an electric field to the sample on the sensing element, the electric field being configured so as to cause movement of the analyte towards the capture species.

* * * * *